US011065331B2

(12) United States Patent
Seya et al.

(10) Patent No.: US 11,065,331 B2
(45) Date of Patent: Jul. 20, 2021

(54) IMMUNE ADJUVANT FOR CANCER

(71) Applicant: Advanced Innovation Development Co. Ltd., Chiyoda-ku (JP)

(72) Inventors: Tsukasa Seya, Sapporo (JP); Misako Matsumoto, Sapporo (JP)

(73) Assignee: Advanced Innovation Development Co. Ltd., Chiyoda-ku (JP)

( * ) Notice: Subject to any disclaimer, the term of this patent is extended or adjusted under 35 U.S.C. 154(b) by 16 days.

(21) Appl. No.: 16/320,660

(22) PCT Filed: Jul. 26, 2017

(86) PCT No.: PCT/JP2017/027027

§ 371 (c)(1),
(2) Date: Jan. 25, 2019

(87) PCT Pub. No.: WO2018/021400

PCT Pub. Date: Feb. 1, 2018

(65) Prior Publication Data

US 2019/0160168 A1 May 30, 2019

(30) Foreign Application Priority Data

Jul. 27, 2016 (JP) ............................ JP2016-147657
Apr. 13, 2017 (JP) ............................ JP2017-079445

(51) Int. Cl.

| | |
|---|---|
| ***A61K 39/39*** | (2006.01) |
| ***A61P 35/00*** | (2006.01) |
| ***A61P 31/04*** | (2006.01) |
| ***A61P 33/02*** | (2006.01) |
| ***A61P 31/06*** | (2006.01) |
| ***A61K 39/12*** | (2006.01) |
| ***A61P 35/02*** | (2006.01) |
| ***A61P 31/18*** | (2006.01) |
| ***A61P 31/16*** | (2006.01) |
| ***A61P 31/12*** | (2006.01) |
| ***A61K 39/395*** | (2006.01) |
| ***A61P 33/06*** | (2006.01) |
| ***A61K 39/02*** | (2006.01) |
| ***A61P 31/22*** | (2006.01) |
| ***A61P 31/00*** | (2006.01) |
| ***C07K 16/28*** | (2006.01) |
| *A61K 39/00* | (2006.01) |

(52) U.S. Cl.

CPC .............. *A61K 39/39* (2013.01); *A61K 39/02* (2013.01); *A61K 39/12* (2013.01); *A61K 39/395* (2013.01); *A61K 39/3955* (2013.01); *A61P 31/00* (2018.01); *A61P 31/04* (2018.01); *A61P 31/06* (2018.01); *A61P 31/12* (2018.01); *A61P 31/16* (2018.01); *A61P 31/18* (2018.01); *A61P 31/22* (2018.01); *A61P 33/02* (2018.01); *A61P 33/06* (2018.01); *A61P 35/00* (2018.01); *A61P 35/02* (2018.01); *C07K 16/2818* (2013.01); *C07K 16/2827* (2013.01); *A61K 2039/505* (2013.01); *A61K 2039/545* (2013.01); *A61K 2039/55561* (2013.01); *A61K 2039/55588* (2013.01); *A61K 2039/55594* (2013.01); *Y02A 50/30* (2018.01)

(58) Field of Classification Search

CPC .............. A61K 39/39; A61K 2039/505; A61K 2039/545; A61K 2039/55561; A61K 2039/55588; A61K 2039/55594; A61K 39/39541; A61K 2039/585; A61K 39/12; A61K 39/395; A61K 39/02; A61K 39/3955; C07K 16/2818; C07K 16/2827; A61P 35/00; A61P 31/04; A61P 33/02; A61P 31/06; A61P 35/02; A61P 31/18; A61P 31/16; A61P 31/12; A61P 33/06; A61P 31/22; A61P 31/00; Y02A 50/30

See application file for complete search history.

(56) References Cited

U.S. PATENT DOCUMENTS

| | | | | |
|---|---|---|---|---|
| 10,105,385 B1 * | 10/2018 | Seya | .................. | A61K 39/0011 |
| 2013/0178611 A1 * | 7/2013 | Seya | .................... | A61K 31/713 536/23.1 |
| 2014/0341978 A1 | 11/2014 | Kim et al. | | |
| 2018/0280425 A1 | 10/2018 | Seya et al. | | |

FOREIGN PATENT DOCUMENTS

| | | |
|---|---|---|
| JP | 2014-527983 A | 10/2014 |
| WO | WO 2008/065752 A1 | 6/2008 |
| WO | WO 2012/014945 A1 | 2/2012 |
| WO | WO 2013/043647 A1 | 3/2013 |

(Continued)

OTHER PUBLICATIONS

International Search Report dated Oct. 3, 2017 in PCT/JP2017/027027 filed Jul. 26, 2017.
Itoh, K. et al., "The Clathrin-Mediated Endocytic Pathway Participates in dsRNA-Induced IFN-β Production," The Journal of Immunology, vol. 181, No. 8, 2008, pp. 5522-5529.
Matsumoto, M. et al., "Defined TLR3-specific adjuvant that induces NK and CTL activation without significant cytokine production in vivo," Nature Communications, vol. 6, No. 6280, 2015, pp. 1-12.
Seya, T. et al., "Priming adjuvant for evoking antitumor immunity," Journal of Clinical and Experimental Medicine, vol. 256, No. 7, Feb. 13, 2016, pp. 811-816 (with partial English language translation).

(Continued)

*Primary Examiner* — J. E. Angell
(74) *Attorney, Agent, or Firm* — Oblon, McClelland, Maier & Neustadt, L.L.P.

(57) ABSTRACT

The present invention relates to a medicament for treating cancer or infectious disease, the medicament comprising an immune checkpoint blockade and an adjuvant composition. More specifically, the present invention relates to a medicament for cancer or infectious diseases, wherein an anti-PD-1 antibody or an anti-PD-L1 antibody is used in combination with a nucleic acid adjuvant composed of a double-stranded RNA and a single-stranded ODN.

17 Claims, 17 Drawing Sheets

Specification includes a Sequence Listing.

(56) References Cited

FOREIGN PATENT DOCUMENTS

| | | | |
|---|---|---|---|
| WO | WO 2016/019472 | A1 | 2/2016 |
| WO | WO 2016/088784 | A1 | 6/2016 |

OTHER PUBLICATIONS

Extended European Search Report dated Jan. 14, 2020 in European Patent Application No. 17834402.4, 11 pages.

Lu, H., "TLR agonists for cancer immunotherapy: tipping the balance between the immune stimulatory and inhibitory effects", Frontiers in Immunology. vol. 5 No. 83, XP055382589, Jan. 1, 2014, pp. 1-4.

Whiteside, T.L. "Inhibiting the inhibitors: evaluating agents targeting cancer immunosuppression", Expert Opinion on Biological Therapy, vol. 10 No. 7, XP055654492, Apr. 23, 2010, pp. 1019-1035.

* cited by examiner

FIG. 1a-b
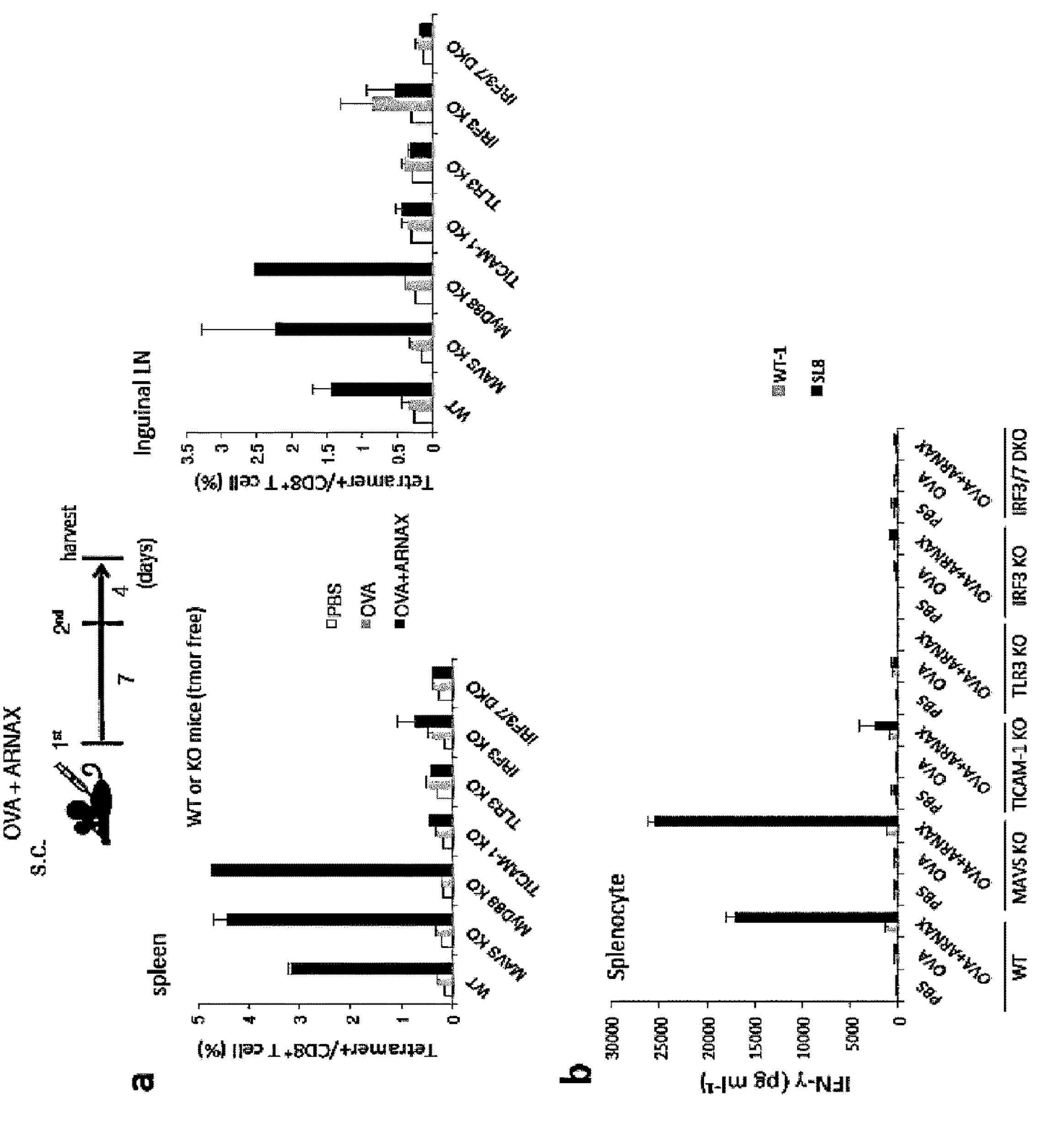

FIG. 3a-c
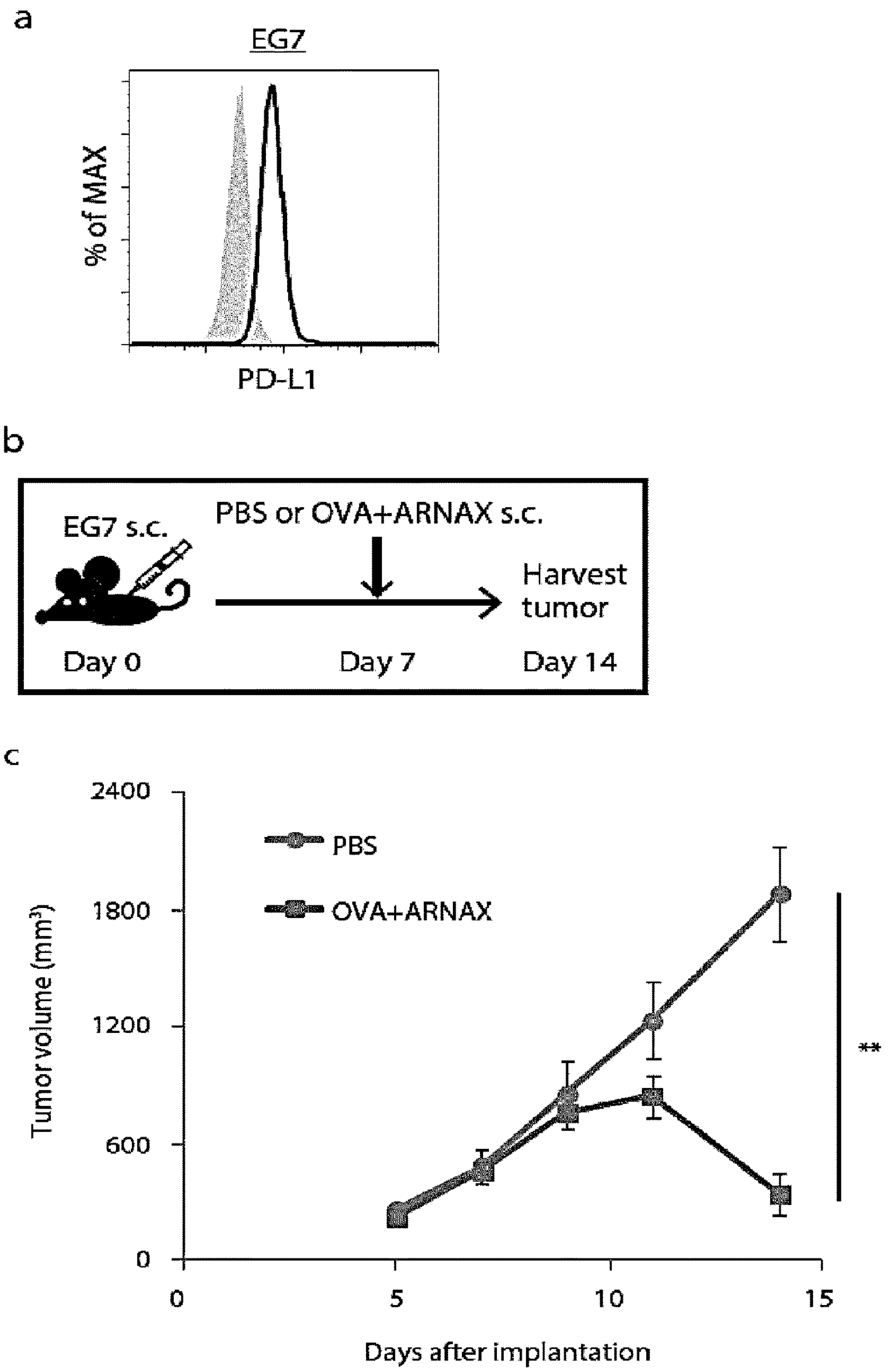

FIG. 3d-f
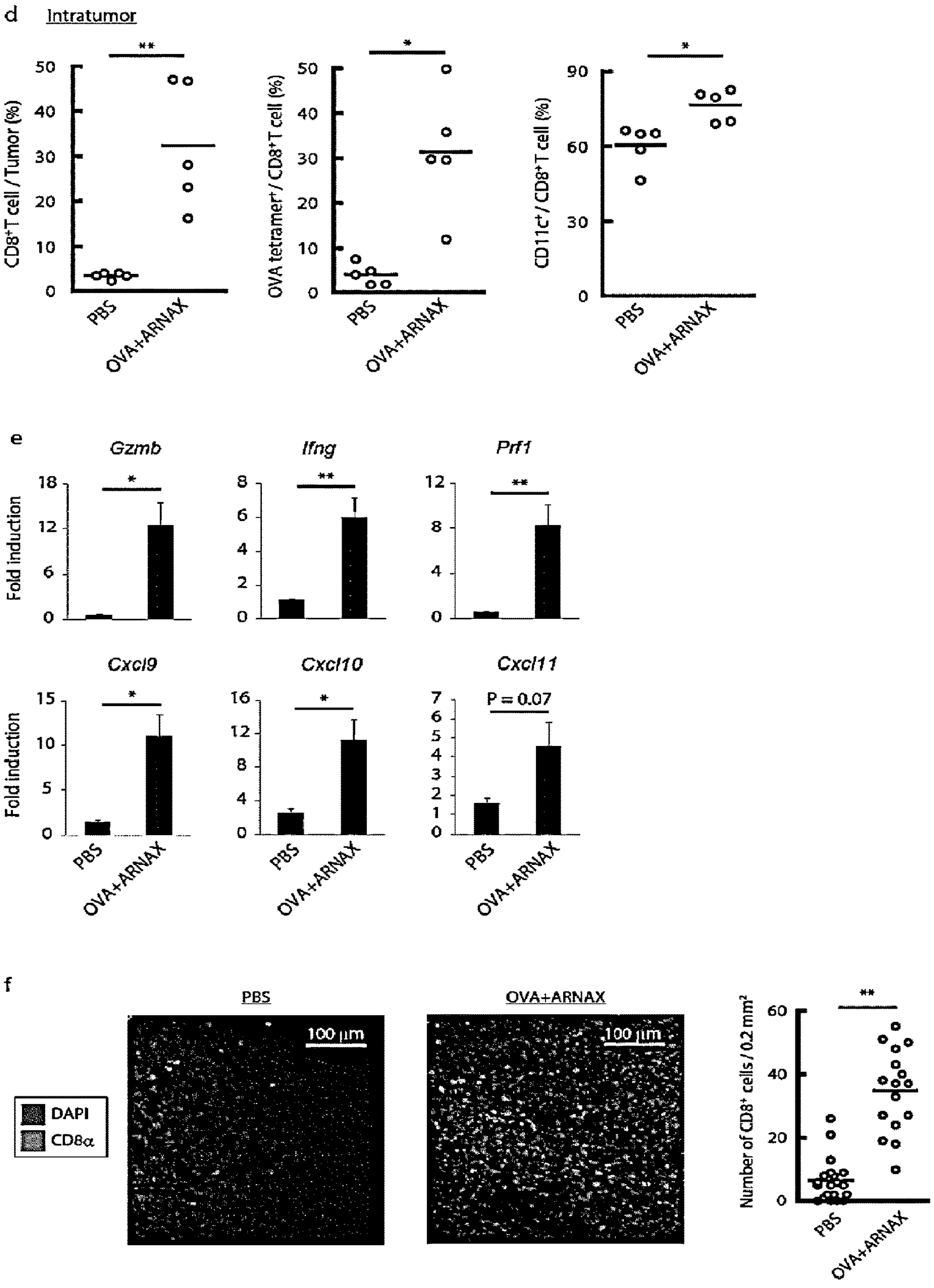

FIG. 4a-c
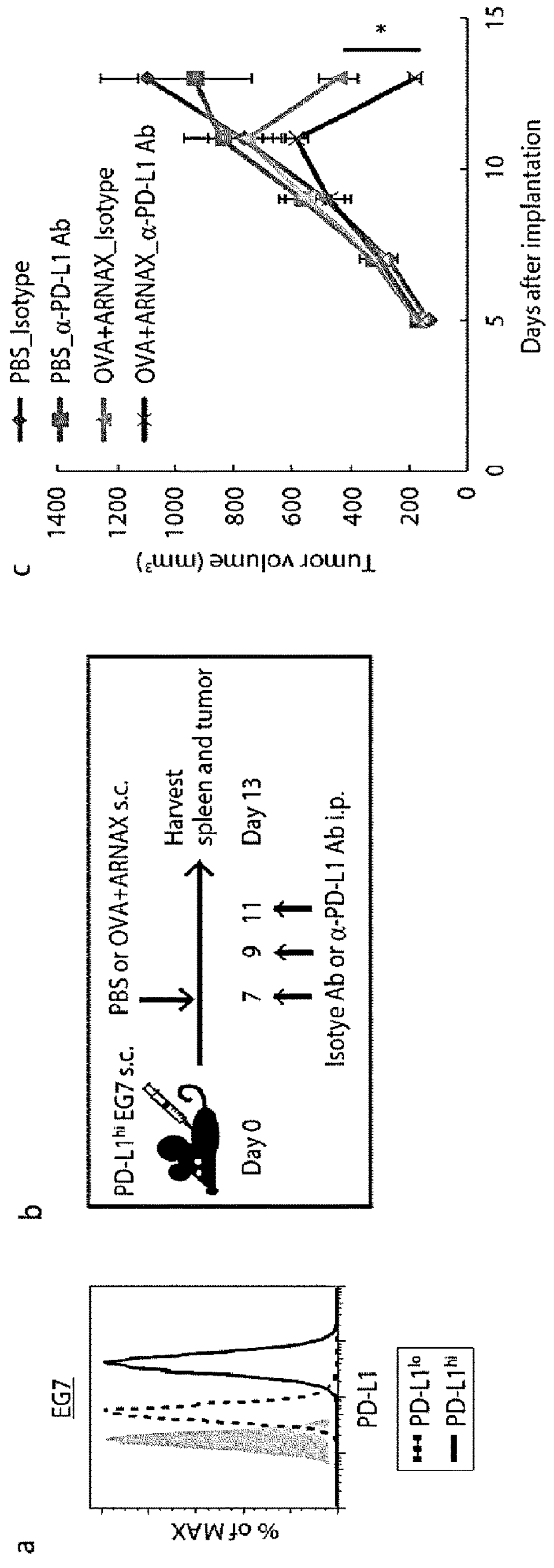

FIG. 6a-e
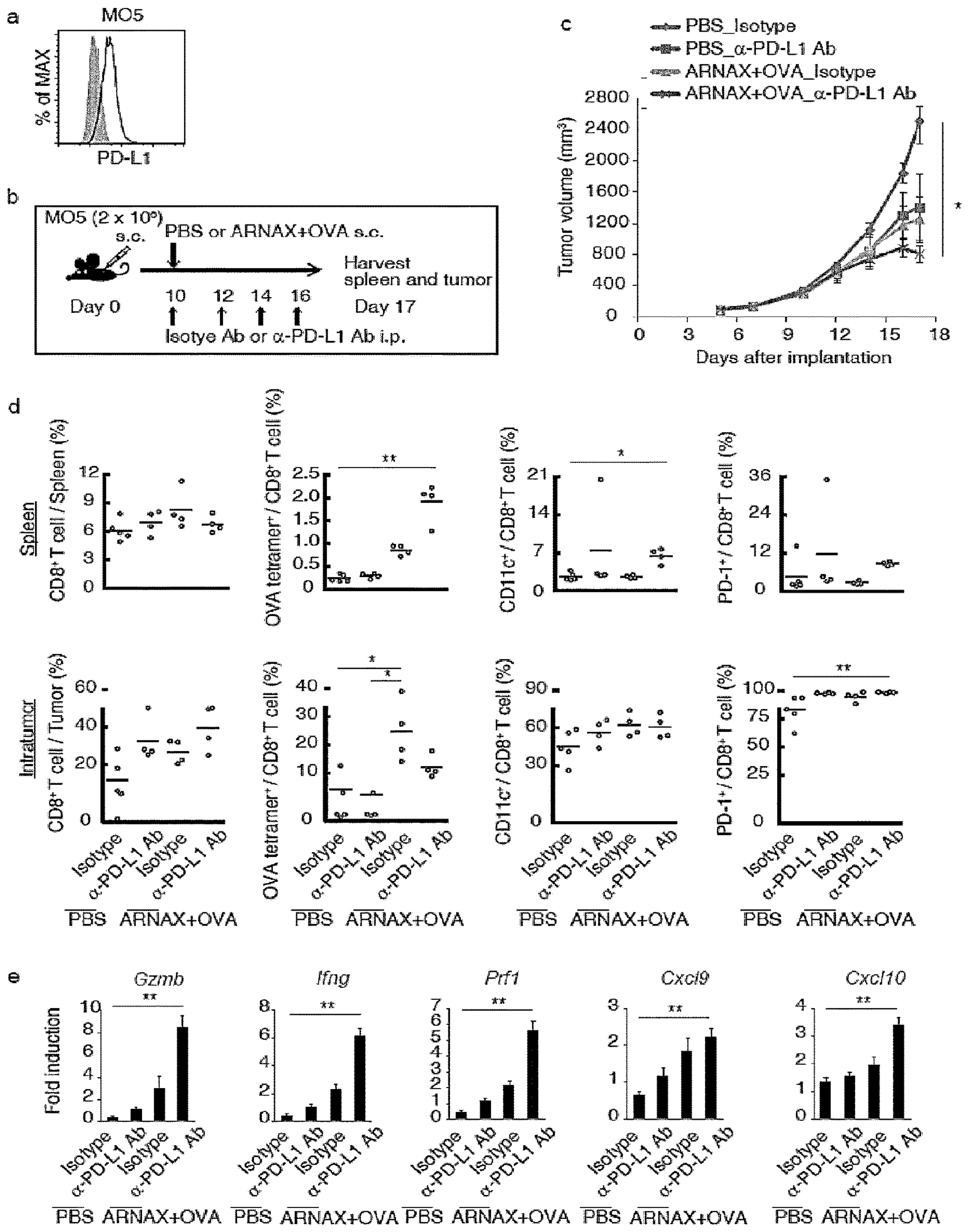

SEQUENCE LISTING

```
<160> NUMBER OF SEQ ID NOS: 47

<210> SEQ ID NO 1
<211> LENGTH: 1152
<212> TYPE: RNA
```

<213> ORGANISM: Measles virus

<400> SEQUENCE: 1
accagacaaa gcugggaaua gaaacuucgu auuuucaaag uuuucuuuaa uauauugcaa 60 auaaaugccua accaccuagg gcaggauuag gguuccggag uucaaccaau uaguccuuaa 120
ucagggcacu guauccgacu aacuuauacc auucuuuggu cuccuugacu guuaccuuaa 180
aaacccacuc acguuucaaa ccccccguca uaauaaucug uuucucugac uuggauagau 240
ucuuaacgaa gauauucugg uguaagucua guaucagaua gccggacuug agauucugga 300
uaaacuuauu uaucaacuuu cuguucccgg aguaaagaag aaugugcccc caaaauuugc 360
gggugauccu agauauaagu ucucguugcc ugcuacuuac caauacgggg uaagcgugga 420
acaucccuug uugacuucuu ugguugucuu ugaaucuugc caacucccug uagaggauga 480
guauagaauu aagcaaucca ucuugcccug aggcaacauc augguggauc aauucuuugc 540
acagcuuagg uccguuaauu gccaacccgc aauugaucag caccugcucu auaggaguaa 600
guuuuuucag aguaggauug auaucaccuc uacuaacugc gucucccaca auugcuugua 660
ugcagcuuag uugcuuaaug gauaggaugu gaccuauaag uccaggugaa guccucacag 720
augauucaau uaucugcugc uuaaucuuuu caggauucau uagccgguua gccuugagau 780
cugucauaac caaauaagau ucaguagaua ugaaguugcu guaucuaggg uauacaaggu 840
ucacuucucu auaaugagac ccuacauaac uuauaaaucc cugaacaaaa uccccgcuga 900
aaggcauaag cuuaaucacc aguauugauc cuauuuugcc caggagcaga gccaucgaua 960
agauggcugc caauuccucu agcuucucua uaguaucuuu guuaggcaag uuagucggau 1020
acagugcccu gauuaaggac uaauugguug aacuccggaa cccuaauccu gcccuaggug 1080
guuaggcauu auuugcaaua uauuaaagaa aacuuugaaa auacgaaguu ucuauuccca 1140
gcuuugucug gu 1152

<210> SEQ ID NO 2
<211> LENGTH: 58
<212> TYPE: RNA
<213> ORGANISM: Measles virus

<400> SEQUENCE: 2
ggauacagug cccugauuaa ggacuaauug guugaacucc ggaacccuaa uccugccc 58

<210> SEQ ID NO 3
<211> LENGTH: 79
<212> TYPE: RNA
<213> ORGANISM: Measles virus

<400> SEQUENCE: 3
cccggugguu aggcauuauu ugcaauauau uaaagaaaac uuugaaaaua cgaaguuucu 60
auucccagcu uugucuggu 79

<210> SEQ ID NO 4
<211> LENGTH: 139
<212> TYPE: RNA
<213> ORGANISM: Measles virus

<400> SEQUENCE: 4
cccggauaca gugcccugau uaaggacuaa uugguugaac uccggaaccc uaauccugcc 60
cuaggugguu aggcauuauu ugcaauauau uaaagaaaac uuugaaaaua cgaaguuucu 120
auucccagcu uugucuggu 139

<210> SEQ ID NO 5
<211> LENGTH: 79
<212> TYPE: RNA
<213> ORGANISM: Measles virus
<400> SEQUENCE: 5
ggugguuagg cauuauuugc aauauauuaa agaaaacuuu gaaaauacga aguuucuauu 60
cccagcuuug ucuggucc c 79

<210> SEQ ID NO 6
<211> LENGTH: 139
<212> TYPE: RNA
<213> ORGANISM: Measles virus
<400> SEQUENCE: 6
ggauacagug cccugauuaa ggacuaauug guugaacucc ggaacccuaa uccugcccua 60
ggugguuagg cauuauuugc aauauauuaa agaaaacuuu gaaaauacga aguuucuauu 120
cccagcuuug ucuggucc c 139

<210> SEQ ID NO 7
<211> LENGTH: 99
<212> TYPE: RNA
<213> ORGANISM: Measles virus
<400> SEQUENCE: 7
ggaacccuaa uccugcccua ggugguuagg cauuauuugc aauauauuaa agaaaacuuu 60
gaaaauacga aguuucuauu cccagcuuug ucuggucc c 99

<210> SEQ ID NO 8
<211> LENGTH: 110
<212> TYPE: RNA
<213> ORGANISM: Measles virus
<400> SEQUENCE: 8
gguugaacuc cggaacccua auccugcccu aggugguuag gcauuauuug caauauauua 60
aagaaaacuu ugaaaauacg aaguuucuau ucccagcuuu gucuggucc c 110

<210> SEQ ID NO 9
<211> LENGTH: 119
<212> TYPE: RNA
<213> ORGANISM: Measles virus
<400> SEQUENCE: 9
ggacuaauug guugaacucc ggaacccuaa uccugcccua ggugguuagg cauuauuugc 60
aauauauuaa agaaaacuuu gaaaauacga aguuucuauu cccagcuuug ucuggucc c 119

<210> SEQ ID NO 10
<211> LENGTH: 73
<212> TYPE: RNA
<213> ORGANISM: Measles virus
<400> SEQUENCE: 10
ggauacagug cccugauuaa ggacuaauug guugaacucc ggaacccuaa uccugcccua 60
ggugguuagg cau 73

<210> SEQ ID NO 11
<211> LENGTH: 140
<212> TYPE: RNA

-continued

<213> ORGANISM: Measles virus

<400> SEQUENCE: 11
accagacaaa gcugggaaua gaaacuucgu auuuucaaag uuuucuuuaa uauauugcaa 60 auaaaugccua accaccuagg gcaggauuag gguuccggag uucaaccaau uaguccuuaa 120
ucagggcacu guauccgacu 140

<210> SEQ ID NO 12
<211> LENGTH: 25
<212> TYPE: DNA
<213> ORGANISM: Artificial Sequence
<220> FEATURE:
<223> OTHER INFORMATION: Synthetic DNA(ODN M362)

<400> SEQUENCE: 12
tcgtcgtcgt tcgaacgacg ttgat 25

<210> SEQ ID NO 13
<211> LENGTH: 24
<212> TYPE: DNA
<213> ORGANISM: Artificial Sequence
<220> FEATURE:
<223> OTHER INFORMATION: Synthetic DNA(ODN 2006)

<400> SEQUENCE: 13
tcgtcgtttt gtcgttttgt cgtt 24

<210> SEQ ID NO 14
<211> LENGTH: 20
<212> TYPE: DNA
<213> ORGANISM: Artificial Sequence
<220> FEATURE:
<223> OTHER INFORMATION: Synthetic DNA(ODN 1668)

<400> SEQUENCE: 14
tccatgacgt tcctgatgct 20

<210> SEQ ID NO 15
<211> LENGTH: 20
<212> TYPE: DNA
<213> ORGANISM: Artificial Sequence
<220> FEATURE:
<223> OTHER INFORMATION: Synthetic DNA(ODN 1826)

<400> SEQUENCE: 15
tccatgacgt tcctgacgtt 20

<210> SEQ ID NO 16
<211> LENGTH: 22
<212> TYPE: DNA
<213> ORGANISM: Artificial Sequence
<220> FEATURE:
<223> OTHER INFORMATION: Synthetic DNA(ODN 2007)

<400> SEQUENCE: 16
tcgtcgttgt cgttttgtcg tt 22

<210> SEQ ID NO 17
<211> LENGTH: 23
<212> TYPE: DNA
<213> ORGANISM: Artificial Sequence
<220> FEATURE:
<223> OTHER INFORMATION: Synthetic DNA(ODN BW006)

<400> SEQUENCE: 17
tcgacgttcg tcgttcgtcg ttc 23

<210> SEQ ID NO 18
<211> LENGTH: 22
<212> TYPE: DNA
<213> ORGANISM: Artificial Sequence
<220> FEATURE:
<223> OTHER INFORMATION: Synthetic DNA(ODN 2395)

<400> SEQUENCE: 18
tcgtcgtttt cggcgcgcgc cg 22

<210> SEQ ID NO 19
<211> LENGTH: 25
<212> TYPE: DNA
<213> ORGANISM: Artificial Sequence
<220> FEATURE:
<223> OTHER INFORMATION: Synthetic DNA(ODN M362 control)

<400> SEQUENCE: 19
tgctgctgct tgcaagcagc ttgat 25

<210> SEQ ID NO 20
<211> LENGTH: 25
<212> TYPE: DNA
<213> ORGANISM: Artificial Sequence
<220> FEATURE:
<223> OTHER INFORMATION: Synthetic DNA(ODN M362 control_TpC substitute)

<400> SEQUENCE: 20
ttcttcttct ttcaatcatc ttgat 25

<210> SEQ ID NO 21
<211> LENGTH: 25
<212> TYPE: DNA
<213> ORGANISM: Artificial Sequence
<220> FEATURE:
<223> OTHER INFORMATION: Synthetic DNA(ODN M362 control_CpC substitute)

<400> SEQUENCE: 21
tcctcctcct tccaaccacc ttgat 25

<210> SEQ ID NO 22
<211> LENGTH: 24
<212> TYPE: DNA
<213> ORGANISM: Artificial Sequence
<220> FEATURE:
<223> OTHER INFORMATION: Synthetic DNA(ODN 2006 control)

<400> SEQUENCE: 22
tgctgctttt gtgcttttgt gctt 24

<210> SEQ ID NO 23
<211> LENGTH: 24
<212> TYPE: DNA
<213> ORGANISM: Artificial Sequence
<220> FEATURE:
<223> OTHER INFORMATION: Synthetic DNA(ODN 2006 control_TpC substitute)

<400> SEQUENCE: 23
ttcttctttt gttcttttgt tctt 24

<210> SEQ ID NO 24
<211> LENGTH: 24
<212> TYPE: DNA

-continued

<213> ORGANISM: Artificial Sequence
<220> FEATURE:
<223> OTHER INFORMATION: Synthetic DNA(ODN 2006 control_CpC substitute)

<400> SEQUENCE: 24
tcctcctttt gtccttttgt cctt 24

<210> SEQ ID NO 25
<211> LENGTH: 22
<212> TYPE: DNA
<213> ORGANISM: Artificial Sequence
<220> FEATURE:
<223> OTHER INFORMATION: Synthetic DNA(ODN 2007 control)

<400> SEQUENCE: 25
tgctgcttgt gcttttgtgc tt 22

<210> SEQ ID NO 26
<211> LENGTH: 22
<212> TYPE: DNA
<213> ORGANISM: Artificial Sequence
<220> FEATURE:
<223> OTHER INFORMATION: Synthetic DNA(ODN 2007 control_TpC substitute)

<400> SEQUENCE: 26
ttcttcttgt tcttttgttc tt 22

<210> SEQ ID NO 27
<211> LENGTH: 22
<212> TYPE: DNA
<213> ORGANISM: Artificial Sequence
<220> FEATURE:
<223> OTHER INFORMATION: Synthetic DNA(ODN 2007 control_CpC substitute)

<400> SEQUENCE: 27
tcctccttgt ccttttgtcc tt 22

<210> SEQ ID NO 28
<211> LENGTH: 23
<212> TYPE: DNA
<213> ORGANISM: Artificial Sequence
<220> FEATURE:
<223> OTHER INFORMATION: Synthetic DNA(ODN BW006 control)

<400> SEQUENCE: 28
tgcagcttgc tgcttgctgc ttc 23

<210> SEQ ID NO 29
<211> LENGTH: 23
<212> TYPE: DNA
<213> ORGANISM: Artificial Sequence
<220> FEATURE:
<223> OTHER INFORMATION: Synthetic DNA(ODN BW006 control_TpC substitute)

<400> SEQUENCE: 29
ttcatctttc ttctttcttc ttc 23

<210> SEQ ID NO 30
<211> LENGTH: 23
<212> TYPE: DNA
<213> ORGANISM: Artificial Sequence
<220> FEATURE:
<223> OTHER INFORMATION: Synthetic DNA(ODN BW006 control_CpC substitute)

<400> SEQUENCE: 30
tccaccttcc tccttcctcc ttc 23

-continued

<210> SEQ ID NO 31
<211> LENGTH: 22
<212> TYPE: DNA
<213> ORGANISM: Artificial Sequence
<220> FEATURE:
<223> OTHER INFORMATION: Synthetic DNA(ODN 2395 control)

<400> SEQUENCE: 31
tgctgctttt gggggcccc cc 22

<210> SEQ ID NO 32
<211> LENGTH: 22
<212> TYPE: DNA
<213> ORGANISM: Artificial Sequence
<220> FEATURE:
<223> OTHER INFORMATION: Synthetic DNA(ODN 2395 control_TpC substitute)

<400> SEQUENCE: 32
ttcttctttt gggggtcccc cc 22

<210> SEQ ID NO 33
<211> LENGTH: 22
<212> TYPE: DNA
<213> ORGANISM: Artificial Sequence
<220> FEATURE:
<223> OTHER INFORMATION: Synthetic DNA(ODN 2395 control_CpC substitute)

<400> SEQUENCE: 33
tcctcctttt gggggccccc cc 22

<210> SEQ ID NO 34
<211> LENGTH: 20
<212> TYPE: DNA
<213> ORGANISM: Artificial Sequence
<220> FEATURE:
<223> OTHER INFORMATION: Synthetic DNA(ODN 1668 control)

<400> SEQUENCE: 34
tccatgagct tcctgatgct 20

<210> SEQ ID NO 35
<211> LENGTH: 20
<212> TYPE: DNA
<213> ORGANISM: Artificial Sequence
<220> FEATURE:
<223> OTHER INFORMATION: Synthetic DNA(ODN 1668 control_TpC substitute)

<400> SEQUENCE: 35
tccatgatct tcctgattct 20

<210> SEQ ID NO 36
<211> LENGTH: 20
<212> TYPE: DNA
<213> ORGANISM: Artificial Sequence
<220> FEATURE:
<223> OTHER INFORMATION: Synthetic DNA(ODN 1668 control_CpC substitute)

<400> SEQUENCE: 36
tccatgacct tcctgatcct 20

<210> SEQ ID NO 37
<211> LENGTH: 20
<212> TYPE: DNA
<213> ORGANISM: Artificial Sequence
<220> FEATURE:

-continued

```
<223> OTHER INFORMATION: Synthetic DNA(ODN 1826 control)

<400> SEQUENCE: 37

tccatgagct tcctgagctt                                                20


<210> SEQ ID NO 38
<211> LENGTH: 20
<212> TYPE: DNA
<213> ORGANISM: Artificial Sequence
<220> FEATURE:
<223> OTHER INFORMATION: Synthetic DNA(ODN 1826 control_TpC substitute)

<400> SEQUENCE: 38

tccatgatct tcctgatctt                                                20


<210> SEQ ID NO 39
<211> LENGTH: 20
<212> TYPE: DNA
<213> ORGANISM: Artificial Sequence
<220> FEATURE:
<223> OTHER INFORMATION: Synthetic DNA(ODN 1826 control_CpC substitute)

<400> SEQUENCE: 39

tccatgacct tcctgacctt                                                20


<210> SEQ ID NO 40
<211> LENGTH: 165
<212> TYPE: DNA
<213> ORGANISM: Artificial Sequence
<220> FEATURE:
<223> OTHER INFORMATION: DNA/RNA chimeric molecule for sense chain
<220> FEATURE:
<221> NAME/KEY: misc_feature
<222> LOCATION: (26)..(165)
<223> OTHER INFORMATION: RNA

<400> SEQUENCE: 40

tgctgctgct tgcaagcagc ttgataccag acaaagcugg gaauagaaac uucguauuuu     60

caaaguuuuc uuuaauauau ugcaaauaau gccuaaccac cuagggcagg auuaggguuc    120

cggaguucaa ccaauuaguc cuuaaucagg gcacuguauc cgacu                    165


<210> SEQ ID NO 41
<211> LENGTH: 140
<212> TYPE: RNA
<213> ORGANISM: Artificial Sequence
<220> FEATURE:
<223> OTHER INFORMATION: Synthetic RNA for antisense chain

<400> SEQUENCE: 41

agucggauac agugcccuga uuaaggacua auugguugaa cuccggaacc cuaauccugc     60

ccuagguggu uaggcauuau uugcaauaua uuaaagaaaa cuuugaaaau acgaaguuuc    120

uauucccagc uuugucuggu                                                140


<210> SEQ ID NO 42
<211> LENGTH: 145
<212> TYPE: DNA
<213> ORGANISM: Artificial Sequence
<220> FEATURE:
<223> OTHER INFORMATION: DNA/RNA chimeric molecule for sense chain

<400> SEQUENCE: 42

tgctgctgct tgcaagcagc ttgataauag aaacuucgua uuuucaaagu uuucuuuaau     60

auauugcaaa uaaugccuaa ccaccuaggg caggauuagg guuccggagu ucaaccaauu    120
```

-continued

```
aguccuuaau cagggcacug uaucc                                          145


<210> SEQ ID NO 43
<211> LENGTH: 120
<212> TYPE: RNA
<213> ORGANISM: Artificial Sequence
<220> FEATURE:
<223> OTHER INFORMATION: Synthetic RNA for antisense chain

<400> SEQUENCE: 43

ggauacagug cccugauuaa ggacuaauug guugaacucc ggaacccuaa uccugcccua     60

ggugguuagg cauuauuugc aauauauuaa agaaaacuuu gaaaauacga aguuucuauu    120


<210> SEQ ID NO 44
<211> LENGTH: 145
<212> TYPE: DNA
<213> ORGANISM: Artificial Sequence
<220> FEATURE:
<223> OTHER INFORMATION: DNA/RNA chimeric molecule for sense chain

<400> SEQUENCE: 44

tgctgctgct tgcaagcagc ttgataauag aaacuucgua uuuucaaagu uuucuuuaau     60

auauuaauag aaacuucgua uuuucaaagu uuucuuuaau auauuaauag aaacuucgua    120

uuuucaaagu uuucuuuaau auauu                                          145


<210> SEQ ID NO 45
<211> LENGTH: 120
<212> TYPE: RNA
<213> ORGANISM: Artificial Sequence
<220> FEATURE:
<223> OTHER INFORMATION: Synthetic RNA for antisense chain

<400> SEQUENCE: 45

aauauauuaa agaaaacuuu gaaaauacga aguuucuauu aauauauuaa agaaaacuuu     60

gaaaauacga aguuucuauu aauauauuaa agaaaacuuu gaaaauacga aguuucuauu    120


<210> SEQ ID NO 46
<211> LENGTH: 155
<212> TYPE: DNA
<213> ORGANISM: Artificial Sequence
<220> FEATURE:
<223> OTHER INFORMATION: DNA/RNA chimeric molecule for sense chain

<400> SEQUENCE: 46

tgctgctgct tgcaagcagc ttgataccag acaaagcugg gaauagaaac uucguauuuu     60

caaaguuuuc uuuaauauau ugcaaauaau gccuaaccac cuagggcagg auuaggguuc    120

cggaguucaa ccaauuaguc cuuaaucagg gcacu                               155


<210> SEQ ID NO 47
<211> LENGTH: 130
<212> TYPE: RNA
<213> ORGANISM: Artificial Sequence
<220> FEATURE:
<223> OTHER INFORMATION: Synthetic RNA for antisense chain

<400> SEQUENCE: 47

agugcccuga uuaaggacua auugguugaa cuccggaacc cuaauccugc ccuaggugguu     60

uaggcauuau uugcaauaua uuaaagaaaa cuuugaaaau acgaaguuuc uauucccagc    120

uuugucuggu                                                           130
```

IMMUNE ADJUVANT FOR CANCER

TECHNICAL FIELD

Related Application

This application claims priority based on Japanese Patent Application Nos. 2016-147657 (filed on Jul. 27, 2016) and 2017-079445 (filed on Apr. 13, 2017), the contents of which are therein incorporated by reference.

Technical Field

The present invention relates to use of an immune checkpoint blockade in combination with an adjuvant composition. More specifically, the present invention relates to a novel therapy for cancer or infectious diseases using an anti-PD-1 antibody or an anti-PD-L1 antibody in combination with a nucleic acid adjuvant composed of a double-stranded RNA and a single-stranded ODN.

BACKGROUND ART

Living bodies have innate immune defense systems to eliminate cancerous cells or pathogens, such as bacteria and viruses, when invading into the living bodies. The molecules to control such an immune defense system are called immune checkpoints. It is believed that often cancer cells cleverly avoid from the monitoring by the immune defense system by demonstrating and enhancing the "immune checkpoints".

PD-1 and PD-L1 are representative immune checkpoint molecules. It is verified that antibodies targeting these molecules demonstrate remarkable anticancer effects to a variety of cancer species. These antibodies are currently being developed as medicines. Although it has been reported about PD-1/PD-L1 antibody therapy that metastatic melanoma has achieved a remission of 50% or more while a remission of solid cancers still remains 20 to 30%. This response rate is not sufficient. Moreover, some patients respond to the PD-1 antibody therapy and others do not. This demands the discrimination between the former and latter patients and also development of a therapy for the latter patients who do not respond to the PD-1 antibody therapy.

Vaccine immunotherapy for cancer has been particularly receiving attention as a fourth therapy for cancers which cannot be treated with surgery, anticancer agents, and radiotherapy. Problems of side effects should often be tackled in discovery of anticancer drugs. The vaccine immunotherapy, however, is advantageous in low invasion and low side effects, because cancer cells are selectively attacked using antigens specific to the cancer cells of interest. The vaccine immunotherapy often uses an adjuvant which aids and enhances the effects of the vaccine by reinforcing the antigenicity of the vaccine.

Activation of Toll-like receptors (TLRs) causes the innate immune response by dendritic cells, inducing the production of cytokines and the activation of cell-mediated immunity. Double stranded RNAs such as poly(I:C) serve as a TLR3 ligand and demonstrate strong anticancer effects. Although such double-stranded RNAs have been considered promising as vaccine adjuvants, their clinical applications were given up due to the side effects such as inflammation and cytokine storm.

The present inventors have found a GpC dinucleotide-containing oligodeoxynucleotide (GpC ODN) which inhibits the induction of expression by poly(I:C) of IFN-β via TLR3, and have reported that this GpC ODN is incorporated into cells (Non Patent Literature 1). The present inventors also have reported that a defective interference RNA (diRNA) derived from measles virus has an adjuvant function (Patent Literature 1).

Furthermore, the present inventors have found that a nucleic acid designed based on the GpC ODN and the diRNA reaches TLR3 on endosomes and demonstrate strong adjuvant activity (Patent Literature 2). This adjuvant induces NK/CTL-dependent anticancer activity in a tumor-implanted mice model without inducing inflammatory cytokine overproduction (Patent Literature 3 and Non Patent Literature 2), which leads to an expectation of the application of this adjuvant to an anticancer immune-enhancing vaccine as a non-inflammatory nucleic acid adjuvant having less side effects.

CITATION LIST

Patent Literature

Patent Literature 1: WO2008/065752
Patent Literature 2: WO2012/014945
Patent Literature 3: WO2016/088784

Non Patent Literature

Non Patent Literature 1: Itoh et al., The Journal of Immunology, 2008, vol. 181, No. 8, pp. 5522-5529
Non Patent Literature 2: Matsumoto et al., Nature Communications, 2015, 6:6280

SUMMARY OF INVENTION

Technical Problem

An object of the present invention is to provide a novel immunotherapy for cancer which improves the response rate in PD-1/PD-L1 antibody therapy while maintaining safety.

Solution to Problem

To solve the problem above, remarkable CTL-dependent tumor regression can be induced by use of an anti-PD-L1 antibody in combination with a nucleic acid adjuvant composed of a double-stranded RNA and a single-stranded oligodeoxynucleotide (single-stranded ODN) in tumors where use of the anti-PD-L1 antibody alone is not effective.

The present invention has been completed based on the knowledge above, and relates to the following (1) to (17).

(1) A medicament for treating cancer or infectious disease, comprising an immune checkpoint blockade and an adjuvant composition, wherein the immune checkpoint blockade comprises an anti-PD-1 antibody or an anti-PD-L1 antibody, and the adjuvant composition comprises a nucleic acid adjuvant composed of a double-stranded RNA and a single-stranded oligodeoxynucleotide (single-stranded ODN) consisting of a sequence of a CpG ODN where CpG is replaced with GpC, TpC, or CpC, or a partial sequence thereof having 5 or more bases in length (where the double-stranded RNA functions as a TLR3 ligand, and the single-stranded ODN functions as a delivery molecule to endosomes).

(2) The medicament according to (1), wherein the immune checkpoint blockade is used in combination with the adjuvant composition.

(3) The medicament according to (2), wherein the immune checkpoint blockade and the adjuvant composition are simultaneously or sequentially administrated.

(4) A medicament for treating cancer or infectious disease, the medicament comprising, as an active ingredient, an immune checkpoint blockade comprising an anti-PD-1 antibody or an anti-PD-L1 antibody, wherein the immune checkpoint blockade is used in combination with an adjuvant composition comprising a nucleic acid adjuvant composed of a double-stranded RNA and a single-stranded oligodeoxynucleotide (single-stranded ODN) consisting of a sequence of a CpG ODN where CpG is replaced with GpC, TpC, or CpC, or a partial sequence thereof having 5 or more bases in length.

(5) The medicament according to any one of (1) to (4), wherein the adjuvant composition comprises an antigen molecule selected from the group consisting of bacterial antigens, viral antigens, and cancer antigens.

(6) The medicament according to any one of (1) to (5), wherein the nucleic acid adjuvant comprises a nucleic acid having a non-phosphorylated end.

(7) The medicament according to any one of (1) to (6), wherein the double-stranded RNA is a nucleic acid having a nucleotide sequence having a sequence of continuous 30 or more, preferably 40 or more bases of a nucleotide sequence represented by SEQ ID NO: 1 and having a total length of 100 to 160, preferably 110 to 150, more preferably 120 to 140 bases in length, or is a nucleic acid having a sequence identity of 80% with the sequence and having a TLR3 activation ability, wherein the nucleic acid as the double-stranded RNA includes a nucleic acid comprising 2 to 4 repetitions of a nucleotide sequence having continuous 30 to 80 bases in length of the nucleotide sequence represented by SEQ ID NO: 1, and preferably a nucleic acid comprising 3 repetitions of a nucleotide sequence composed of continuous 30 to 50 bases in length of the nucleotide sequence represented by SEQ ID NO: 1.

(8) The medicament according to any one of (1) to (7), wherein the double-stranded RNA is a nucleic acid having a nucleotide sequence represented by one of SEQ ID NOs: 2 to 11, a nucleic acid having a nucleotide sequence having continuous 100 or more bases, preferably 110 or more bases, more preferably 120 or more bases thereof, or a nucleic acid having a sequence identity of 80% with the sequence and having a TLR3 activation ability.

(9) The medicament according to any one of (1) to (8), wherein the double-stranded RNA is a nucleic acid having a nucleotide sequence represented by SEQ ID NO: 11, a nucleic acid having a nucleotide sequence having continuous 100 or more bases, preferably 110 or more bases, more preferably 120 or more bases thereof, or a nucleic acid having a sequence identity of 80% with the sequence and having a TLR3 activation ability.

(10) The medicament according to any one of (1) to (9), wherein the single-stranded ODN is a nucleic acid consisting of a nucleotide sequence represented by one of SEQ ID NOs: 19 to 39 or a partial sequence thereof having 5 or more bases thereof in length.

(11) The medicament according to any one of (1) to (9), wherein the single-stranded ODN is a nucleic acid consisting of a nucleotide sequence represented by one of sequences No. 19 to 24 or a partial sequence thereof having 5 or more bases in length.

(12) The medicament according to any one of (1) to (11), wherein the single-stranded ODN has 15 to 28 bases in length.

(13) The medicament according to any one of (1) to (12), wherein the single-stranded ODN comprises a nucleotide modified with phosphorothioate.

(14) The medicament according to any one of (1) to (13), wherein the nucleic acid adjuvant is a nucleic acid comprising a sense strand represented by SEQ ID NO: 40 and an antisense strand represented by SEQ ID NO: 41, a nucleic acid comprising a sense strand represented by SEQ ID NO: 42 and an antisense strand represented by SEQ ID NO: 43, or a nucleic acid comprising a sense strand and an antisense strand each having a sequence identity of 80% with the sequence and having adjuvant activity.

(15) The medicament according to any one of (1) to (14), wherein the nucleic acid adjuvant comprises 1) a sense strand represented by SEQ ID NO: 40 and an antisense strand represented by SEQ ID NO: 41,
2) a sense strand represented by SEQ ID NO: 42 and an antisense strand represented by SEQ ID NO: 43,
3) a sense strand represented by SEQ ID NO: 44 and an antisense strand represented by SEQ ID NO: 45, or
4) a sense strand represented by SEQ ID NO: 46 and an antisense strand represented by SEQ ID NO: 47.

(16) An adjuvant composition comprising a nucleic acid adjuvant composed of a double-stranded RNA and a single-stranded oligodeoxynucleotide (single-stranded ODN) consisting of a sequence of a CpG ODN where CpG is replaced with GpC, TpC, or CpC or a partial sequence thereof having 5 or more bases in length, wherein the double-stranded RNA is a nucleic acid comprising 2 to 4 repetitions of a nucleotide sequence having continuous 30 to 80 bases in length of a nucleotide sequence represented by SEQ ID NO: 1, preferably a nucleic acid comprising 3 repetitions of a nucleotide sequence having continuous 30 to 50 bases in length of the nucleotide sequence represented by SEQ ID NO: 1.

(17) A medicament for treating cancer or infectious disease, comprising the adjuvant composition according to (16).

Advantageous Effects of Invention

The present invention can improve the effects of the PD-1/PD-L1 antibody therapy and the response rate. The adjuvant according to the present invention is efficiently taken up into dendritic cells to specifically activate TLR3 and induce NK cells and CTLs without inducing systemic inflammatory cytokine production. Accordingly, unlike other composite immunotherapies, the effects of the PD-1/PD-L1 antibodies are mildly improved without generating side effects such as cytokine storm, resulting in tumor regression.

BRIEF DESCRIPTION OF DRAWINGS

FIG. 1*a* illustrates induction (%) of expression of tumor-specific CTLs in spleens and lymph nodes of lower limbs of mice (wild type (WT) and a variety of knockout (KO) mice) to which PBS (control), OVA, or OVA+ARNAX was subcutaneously administrated.

FIG. 1*b* illustrates IFN-γ production (pg/ml) in spleen cells of mice (wild type (WT) and a variety of knockout (KO) mice) to which PBS (control), OVA, or OVA+ARNAX was subcutaneously administrated.

FIG. 3*a* illustrates the expression of PD-L1 of EG7 cell lines.

FIG. 3*b* illustrates an outline of the protocol of an experiment in Example 3 (antitumor effects in administration of ARNAX and the antigen).

FIG. 3*c* illustrates a change over time of the tumor volume in mice subjected to subdermal transplantation of EG7 cells on day 0. Remarkable tumor regression was observed in mice to which OVA+ARNAX were subcutaneously administrated on day 7 (-●-) while tumor regression was not observed in mice (control) to which PBS was administrated (-■-).

FIG. 3*d* illustrates the proportions of CD8-positive T cells (left), OVA tetramer-positive/CD8-positive T cells (center), and CD11c-positive/CD8-positive T cells (right) in tumors of mice to which PBS (control) or OVA+ARNAX were subcutaneously administrated.

FIG. 3*e* illustrates the results of analysis by quantitating PCR of induction of expression of Gzmb, Ifng, Prf1, Cxcl9, Cxcl10, and Cxcl11 in mice to which PBS (control) or OVA+ARNAX were subcutaneously administrated.

FIG. 3*f* illustrates immunostaining of DAPI and CD8α in tumor tissues of mice to which PBS (control) or OVA+ARNAX were subcutaneously administrated.

FIG. 4*a* illustrates the expression of PD-L1 in comparison between PD-L1 highly expressing EG7 cells lines (solid line) and normal lines (dashed line).

FIG. 4*b* illustrates an outline of the protocol of an experiment in Example 4 (use of ARNAX with an anti-αPD-L1 antibody in combination).

FIG. 4*c* illustrates a change over time of the tumor volume in mice subjected to subdermal transplantation of EG7 cells on day 0, subdermal administration of PBS (control) or OVA+ARNAX on day 7, and then intravenous administration of an anti-mice PD-L1 antibody or an isotype antibody. While tumor regression is not observed in administration (-■-) of the PD-L1 antibody alone, remarkable tumor regression is observed by administration (-x-) of the PD-L1 antibody in combination with OVA+ARNAX, and the effect is higher than that in administration (-▲-) of only OVA+ARNAX.

FIG. 6*a* shows the expression of PD-L1 of MO5 cell lines (solid line).

FIG. 6*b* illustrates an outline of the protocol of an experiment in Example 5 (use of ARNAX in combination with an anti-αPD-L1 antibody).

FIG. 6*c* shows a change over time of the tumor volume in mice subjected to subdermal transplantation of MO5 cells on day 0, subdermal administration of PBS (control) or OVA+ARNAX on day 10, and then intravenous administration of an anti-mice PD-L1 antibody or an isotype antibody. Compared to the administration (-■-) of the PD-L1 antibody alone and the administration (-▲-) of OVA+ARNAX, remarkably great tumor regression is observed in the administration (-X-) of the PD-L1 antibody in combination with OVA+ARNAX.

FIG. 6*d* shows the proportions of CD8-positive T cells (left), OVA tetramer-positive/CD8-positive T cells (left center), CD11c-positive/CD8-positive T cells (right center), PD-1-positive/CD8-positive T cells (right) in spleens and tumors of mice to which PBS (control) or OVA+ARNAX was subcutaneously administrated, and the anti-mice PD-L1 antibody or an isotype antibody was intravenously administrated (the upper row indicates the proportions in the spleens, and the lower row indicates the proportions in the intratumors).

FIG. 6*e* shows the results of analysis by RT-PCR of the induction of expression of Gzmb, Ifng, Prf1, Cxcl9, and Cxcl10 in tumors of mice to which PBS (control) or OVA+ARNAX was subcutaneously administrated, and the anti-mice PD-L1 antibody or isotype antibody was intravenously administrated.

DESCRIPTION OF EMBODIMENTS

Figure 1C:
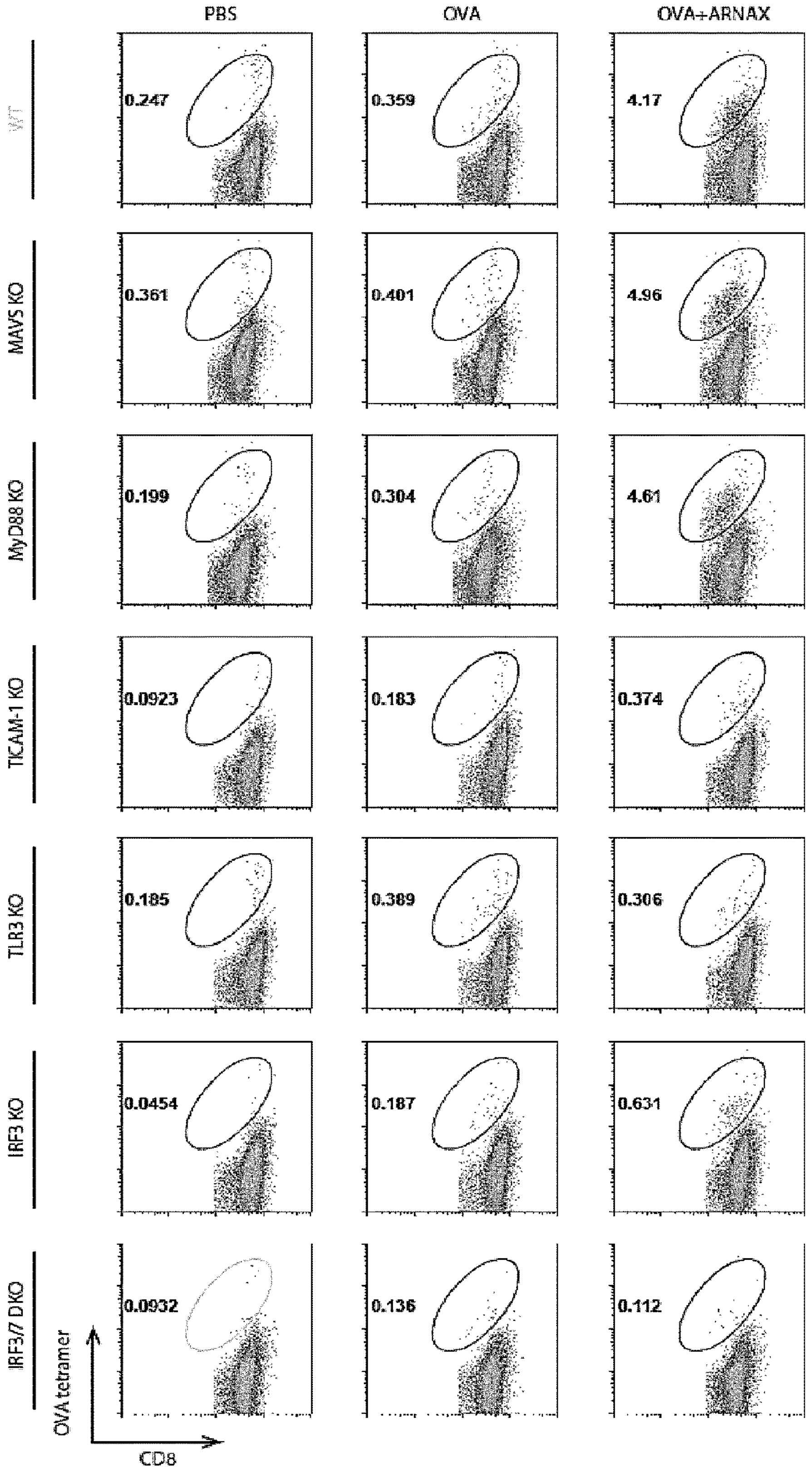
FIG. 1*c* illustrates the results of analysis by flow cytometry of tumor-specific CTLs derived from spleens of mice (wild type (WT) and a variety of knockout (KO) mice) to which PBS (control), OVA, or OVA+ARNAX was subcutaneously administrated.

The present invention relates to a medicament for treating cancer or infectious disease, comprising an immune checkpoint blockade (anti-PD-1 antibody or anti-PD-L1 antibody) and a nucleic acid adjuvant composed of a double-stranded RNA and a single-stranded ODN.

1. Immune Checkpoint Blockade

Molecules which control the natural immune defense system against cancer cells and pathogens such as bacteria and viruses is referred to as immune checkpoints. Examples thereof include PD-1 which expresses on surfaces of effector T cells, PD-L1 and PD-L2 which express on surfaces of tumor cell, CTLA-4 expressing on surfaces of activated T cells or regulatory T cells Treg, and CD80 and CD86 which express on surfaces of dendritic cells. Among these molecules, CTLA-4, CD80, and CD86 functions in a priming phase where sensitized T cells differentiate from naive T cells to $T_{H1}$, $T_{H2}$, and $T_{FH}$ cells, and PD-1, PD-L1, and PD-L2 function in an effector phase where effector cells attack tumor cells.

The term "immune checkpoint blockade" indicates a substance/molecule which inhibits the "immune checkpoints" and controls the natural immune defense system. Representative examples of the "immune checkpoint blockade" include antibodies specific to the immune checkpoints described above (such as anti-PD-1 antibodies, anti-PD-L1 antibodies, and anti-CTLA-4 antibodies).

The "immune checkpoint blockade" used in the present invention is an immune checkpoint blockade which functions in the effector phase, that is, a substance/molecule which inhibits PD-1, PD-L1, and PD-L2. Preferably, the "immune checkpoint blockade" is an anti-PD-1 antibody or an anti-PD-L1 antibody.

"Anti-PD-1 Antibody"

The term "anti-PD-1 antibody" used in the present invention can be any anti-PD-1 antibody which can bind to PD-1 to inhibit the function of the PD-1 as an immune checkpoint. The anti-PD-1 antibody includes those which are already approved as medicaments and are commercially available, and those which are under development. These can be suitably used. Examples of the "anti-PD-1 antibody" include, but should not be limited to, Nivolumab (Opdivo (GSK/Ono Pharmaceutical Co., Ltd.)), a humanized IgG4 antibody Pembrolizumab (MK-3475 (Merck KGaA)), and Pidilizumab (CT-011 (CureTech Ltd.)).

"Anti-PD-L1 Antibody"

The "anti-PD-L1 antibody" used in the present invention can be any anti-PD-L1 antibody which can bind to PD-L1 to inhibit the function of the PD-L1 as an immune checkpoint. The anti-PD-L1 antibody includes those which are already approved as medicaments and are commercially available, and those which are under development. These can be suitably used. Examples of the "anti-PD-L1 antibody" include, but should not be limited to, Atezolizumab (MPDL3280A/RG-7446 (Roche/Chugai Pharmaceutical), Durvalumab (MEDI4736 (AstraZeneca plc)), Avelumab (MSB0010718C (Merck KGaA)), and MED10680/AMP-514.

The antibody may be prepared according to a normal method. In this case, to reduce the heterologous antigenicity against human, the antibody is preferably a chimeric antibody, a humanized antibody, or a fully human antibody. The antibody can be an antibody fragment which can function as an immune checkpoint blockade. Examples of the antibody fragment include $F(ab')_2$, Fab', Fab, Fv, and scFv.

The "immune checkpoint blockade" according to the present invention may contain pharmaceutically acceptable carriers and additives. Examples of such carriers and additives include, but should not be limited to, surfactants, fillers, colorants, fragrances, preservatives, antioxidants, stabilizers, buffers, suspensions, isotonizing agents, fillers, disintegrants, lubricants, fluidity promoters, and flavoring substance. Besides, other carriers usually used can be appropriately used.

Specifically, examples of aqueous carriers include water, ethanol, polyols (such as glycerol, propylene glycol, and polyethylene glycol), vegetable oils such as olive oil, and organic esters such as ethyloleic acid.

Examples of non-aqueous carriers include light silica anhydride, lactose, crystal cellulose, mannitol, starch, carmellose calcium, carmellose sodium, hydroxypropylcellulose, hydroxypropylmethylcellulose, polyvinylacetal diethylaminoacetate, polyvinylpyrrolidone, gelatin, medium chain triglyceride, polyoxyethylene hard castor oil 60, saccharose, carboxymethyl cellulose, corn starch, and inorganic salts.

Examples of the antioxidants include water-soluble antioxidants such as ascorbic acid, cysteine hydrochloride, sodium bisulfate, sodium metabisulfite, and sodium sulfite; lipid-soluble antioxidants, such as ascorbyl dipalmitate, butylated hydroxyanisole (BHA), butylated hydroxytoluene (BHT), lecithin, propyl gallate, and α-tocopherol; and metal chelating agents such as citric acid, ethylenediaminetetraacetic acid (EDTA), sorbitol, tartaric acid, and phosphoric acid.

The "immune checkpoint blockade" according to the present invention can be administrated through any route. Preferred is parenteral administration. Specifically, examples thereof include injection administration, nasal administration, transpulmonary administration, and dermal administration. Examples of the injection administration include intravenous injection, intramuscular injection, intraperitoneal injection, and subdermal injection. The administration method can be appropriately selected according to the age and condition of the patient.

The dose of the "immune checkpoint blockade" according to the present invention is appropriately determined according to the purpose of use, the administration route, and the like. The dose is adjusted so as to obtain an optimal response (such as a therapeutic response) intended. Because the active ingredient is an antibody, the dose is within the range of about 0.0001 to 100 mg/kg, and usually is 0.01 to 5 mg/kg in terms of the weight of the patient. For example, the dose is about 0.3 mg/kg/weight, 1 mg/kg/weight, 3 mg/kg/weight, 5 mg/kg/weight, or 10 mg/kg/weight, or is within the range of 1 to 10 mg/kg. A typical therapeutic method includes administration once a week, administration once every two weeks, administration once every three weeks, administration once every four weeks, administration once a month, administration once every three months, or administration once every three to six months. For example, the dose is 1 mg/kg/weight or 3 mg/kg/weight in the administration through intravenous injection. The number of administrations may be appropriately set according to the condition. The immune checkpoint blockade may be administrated in the form of a single bolus, or aliquots thereof may be administrated several times over time. For example, the immune checkpoint blockade may be administrated 6 times every four weeks, followed by administration every three weeks, may be administrated every three weeks, or may be administrated at 3 mg/kg/weight once, followed by administration at 1 mg/kg/weight every three weeks.

2. Adjuvant Composition 2.1 Nucleic Acid Adjuvant

The "adjuvant composition" according to the present invention comprises a nucleic acid (nucleic acid adjuvant) composed of a double-stranded RNA and a single-stranded oligodeoxynucleotide (single-stranded ODN) delivered to endosomes.

(1) "Double Stranded RNA"

It is known that microorganism-derived double-stranded RNAs activate the natural immunity as ligands to the Toll-like receptor 3 (TLR3). The same phenomenon is also observed in artificially synthesized double-stranded RNAs (Matsumoto M., and T. Seya. 2008. TLR3: Interferon induction by double-stranded RNA including poly(I:C). Adv. Drug Del. Rev. 60: 805-812.). TLR is a type I membrane protein, and recognizes the components derived from viruses and bacteria to induce the response of host defense. TLR3 is a member of the TLR family. TLR3 has an extracellular double-stranded RNA as a ligand, and induces a variety of cellular responses via TICAM-1. TLR3 is localized in endosomes of bone marrow dendritic cells, and is localized on cell surfaces and in endosomes of macrophages and part of epidermal cells. Signals via TLR3 are transmitted from the endosomes of these cells. For this reason, double-stranded RNAs should be taken into the cells.

The microorganism-derived double-stranded RNAs do not act on human genes, and control the natural immunity as a TLR3 ligand. Thus, research about use of such double-stranded RNAs as a vaccine adjuvant has been progressed. The "double-stranded RNA" used in the present invention is such an exogenous (e.g., virus-derived or bacteria-derived) double-stranded RNA, and activates the natural immunity as a TLR3 ligand (i.e., has TLR3 activation ability) without affecting the human endogenous genes.

The "double-stranded RNA" according to the present invention can be synthesized using a template obtained by isolating a dsRNA derived from an RNA virus. Any RNA virus can be used as a target, and can be any of negative-sense single-stranded RNA viruses, positive-sense single-stranded RNA viruses, and double-stranded RNA viruses. Specifically, examples thereof include measles viruses, Sendai viruses, RS viruses, hepatitis C viruses, Polio viruses, and rotaviruses. Preferred are measles viruses, Sendai viruses, and RS viruses of the negative-sense single-stranded RNA viruses, and more preferred are vaccine strains of measles virus, Sendai viruses, and RS viruses.

A laboratory-adapted measles virus strain, i.e., a diRNA (defective interference RNA: SEQ ID NO: 1) derived form an Edmonston (ED) strain is conventionally contained in vaccines, and has established safety to human (Shingai et al., J Immunol. 2007; 179: 6123-6133). The present inventors have found that the diRNA derived from the ED strain has a function as an adjuvant (Itoh et al., op. cit., The Journal of Immunology, 2008; Matsumoto et al. Nat. Commun. 2015), and have verified that the double-stranded RNAs having 59 to 140 bases in length and prepared based on the diRNA are coupled with single-stranded ODNs described later to be efficiently delivered to endosomes, activate only TLR3 without activating intracellular RNA sensors RIG-I and MDA5, and have the effect of tumor regression (WO2012/014945 and WO2016/088784). By capping the 5'-end of the "double-stranded RNA" based on the diRNA derived from the ED strain, the "double-stranded RNA" specifically activates only TLR3 without activating another immune system (such as MDA5/RIG-1). Thus, the "double-stranded RNA" is excellent as a vaccine adjuvant without risks of causing induction of systemic inflammatory cytokines. Accordingly, examples of one preferred form of the "double-stranded RNA" used in the present invention can include the double-stranded RNAs based on the diRNA derived from the ED strain. In addition, double-stranded RNAs derived from other viruses and bacteria can also be used as a TLR3 ligand in the nucleic acid adjuvant according to the present invention.

The "double-stranded RNA" can have any length. For the TLR3 activation ability, the length is preferably about 50 or more base pairs, more preferably about 60 or more base pairs, more preferably about 90 or more base pairs, more preferably about 100 or more bases in length, still more preferably about 110 or more bases, particularly preferably about 120 bases or more in length. The length can have any upper limit. In view of easiness in synthesis, a length up to about 160 base pairs is preferred. Accordingly, the "double-stranded RNA" according to the present invention has a length of preferably about 50 to 160 base pairs, more preferably about 90 to 150 base pairs, more preferably about 100 to 150 base pairs, more preferably about 110 to 140 base pairs, particularly preferably about 120 to 140 base pairs.

The diRNA derived from the ED strain has a nucleotide sequence represented by SEQ ID NO: 1, and forms a double-stranded RNA (diRNA) having a loop structure (Shingai et al., J Immunol. 2007 Nov. 1; 179(9):6123-6133). In the case of design of the "double-stranded RNA" based on the diRNA derived from the ED strain, any portion of the diRNA of the ED strain represented by SEQ ID NO: 1 may be used as the "double-stranded RNA". Preferred are AU-rich regions in view of synthetic efficiency. Examples of such AU-rich regions include sequences of sense strands such as positions 17 to 78, positions 101 to 164, and positions 216 to 269 of SEQ ID NO: 1. These are all preferred regions in view of synthetic efficiency, and the function as the TLR3 ligand is not limited to these regions.

In the patent application described above (WO2012/014945), double-stranded RNAs are prepared which have the following nucleotide sequences of the diRNA of the ED strain represented by SEQ ID NO: 1, respectively, and the activities are verified.

nucleotide sequence of positions 1017 to 1074 (SEQ ID NO: 2), nucleotide sequence of positions 1077 to 1152 having three cytosines added to its 5'-end (SEQ ID NO: 3)

nucleotide sequence of positions 1017 to 1152 having three cytosines added to its 5'-end (SEQ ID NO: 4)

nucleotide sequence of positions 1077 to 1152 having three cytosines added to its 3'-end (SEQ ID NO: 5)

nucleotide sequence of positions 1017 to 1152 having three cytosines added to its 3'-end (SEQ ID NO: 6)

nucleotide sequence of positions 1057 to 1152 having three cytosines added to its 3'-end (SEQ ID NO: 7)

nucleotide sequence of positions 1046 to 1152 having three cytosines added to its 3'-end (SEQ ID NO: 8)

nucleotide sequence of positions 1037 to 1152 having three cytosines added to its 3'-end (SEQ ID NO: 9)

nucleotide sequence of positions 1017 to 1089 (SEQ ID NO: 10).

In the patent application (WO2016/088784), a double-stranded RNA having a nucleotide sequence of positions 1 to 140 (SEQ ID NO: 11) of the diRNA of the ED strain represented by SEQ ID NO: 1 is prepared, and the activity is verified. Considering that the diRNA forms a stem loop, it can be understood that the sequence represented by SEQ ID NO: 11 is a region complementary to the sequences represented by SEQ ID NOs: 2 to 9.

Accordingly, the nucleic acids (double-stranded RNAs) having a nucleotide sequence having continuous 30 to 160 bases in length of the nucleotide sequence represented by SEQ ID NO: 1 can be used as the "double-stranded RNA" according to the present invention. In view of the synthetic efficiency, nucleic acids (double-stranded RNAs) can be suitably used, which contain continuous 30 or more bases, preferably 40 or more bases (may have (a) repetition(s)) of positions 17 to 78, 101 to 164, and 216 to 269 of the nucleotide sequence represented by SEQ ID NO: 1 and has a total length of 100 to 160 bases in length, preferably 110 to 150 bases in length, more preferably 120 to 140 bases in length. The "double-stranded RNA" may be those having 2 to 4 repetitions of a partial sequence of the nucleotide sequence represented by SEQ ID NO: 1. For example, those containing continuous 120 bases in length of positions 17 to 136 of SEQ ID NO: 1 (SEQ ID NO: 42 (sense), SEQ ID NO: (antisense)), and those having 3 repetitions of continuous 40 bases in length of positions 17 to 56 of the nucleotide sequence represented by SEQ ID NO: 1 (SEQ ID NO: 44 (sense) and SEQ ID NO: 45 (antisense)) can also be used.

One example thereof includes a nucleic acid having a nucleotide sequence represented by one of SEQ ID NOs: 2 to 11. Among these, the present inventors have verified the effect of tumor regression in vivo in the nucleic acids having a nucleotide sequence represented by SEQ ID NO: 11 and a partial sequence thereof.

Considering the functions and the structures of the "double-stranded RNA" according to the present invention and the diRNA derived from the ED strain, not only the nucleic acids (double-stranded RNAs) having the nucleotide sequences represented by SEQ ID NOs: 2 to 11 but also double-stranded RNAs having a nucleotide sequence having continuous 100 or more bases, preferably 110 or more bases, more preferably 120 or more bases of the diRNA can be used. In addition, double-stranded RNAs having a nucleotide sequence having a sequence identity of 80%, sequence identity, preferably 85%, more preferably 90%, still more preferably 95% with the sequence can also be used as the "double-stranded RNA" according to the present invention as long as they have the TLR3 activation ability. If the "double-stranded RNA" contains a repetition of a partial sequence, the sequence identity is defined as a numeric value obtained from comparison between the partial sequence and the sequence corresponding to the partial sequence.

The "double-stranded RNA" according to the present invention which can be used include double-stranded RNAs having the nucleotide sequences represented by SEQ ID NOs: 2 to 11 or nucleotide sequences thereof having continuous 100 or more bases, preferably 110 or more bases, still more preferably 120 or more bases where 1 to 10, preferably 1 to 6, more preferably 1 to 3 bases are deleted, substituted, inserted, or added, as long as they have the TLR3 activation ability.

The TLR3 activation ability can be readily verified as described in Example 2 of WO2012/014945: a human TLR3 expressing plasmid together with a reporter plasmid containing an IFN-β promotor is transfected into cells, and a double-stranded RNA is added to the culture solution of the prepared cells to observe an increase in the reporter activity. Accordingly, any "double-stranded RNA" other than those represented by SEQ ID NOs: 2 to 11 can be used. Persons skilled in the art could easily obtain other "double-stranded RNAs" used in the present invention from the nucleotide sequence of a virus- or bacteria-derived dsRNA as represented by SEQ ID NO: 1, the descriptions in WO2012/014945 and WO2016/088784, and technical common knowledge in the field.

(2) Single-Stranded Oligodeoxynucleotide (Single-Stranded ODN)

TLR9 recognizes non-methylated CpG motives of virus DNAs and bacteria DNAs. Signaling via TLR9 is highly efficiently performed by a short synthetic oligodeoxynucleotide (ODN). This ODN contains a CpG motif specific to bacteria and virus genes, and is known as a "CpG ODN" in the field. It is known that the CpG ODN is delivered to endosomes of dendritic cells to function as a TLR9 ligand, and is useful as a strong vaccine adjuvant or an antibody production enhancer. On the other hand, the CpG ODN strongly induces MyD88-dependent cytokines (particularly, IFN-γ) to cause Th2 response. The CpG ODN is classified into three types: a type A is an activator of NK cells which strongly induce IFNα, a type B is an activator of B cells which weakly induces IFNα, and a type C has both of the action of the type B and that of the type A. The "single-stranded ODN" according to the present invention is preferably a type GpC from which the cytokine inducing activity of the CpG is removed, and is based on the GpC ODN of the type B or C.

The present inventors have verified that ODNs (GpC ODNs) where CpG is replaced with GpC in the CpG ODN and ODNs where the GpC is replaced with TpC or CpC are also delivered to endosomes in the patent application described above (WO2012/014945). Furthermore, the present inventors have verified that the nucleic acids having a partial sequence of the ODN having 5 or more bases in length are also delivered to endosomes.

The ODNs where CpG is replaced with GpC, TcP, or CPC are delivered to the endosomes of the dendritic cells, but such ODNs have no TLR9 agonist activity. Thus, these ODNs do not induce unnecessary immune response. Namely, the "single-stranded ODN" used in the present invention is a single-stranded ODN delivered to endosomes without the TLR9 agonist activity.

The CpG ODN is commercially available as a TLR9 agonist and the GpC ODN is commercially available as its control (because it has no TLR9 agonist activity). These ODNs can be suitably used in the present invention. The CpG ODNs (type B or C) and their GpC ODNs (control) available from Invivogen and their sequences are listed below (http://www.invivogen.com/tlr9-agonist).

TABLE 1

| | | |
|---|---|---|
| CpG ODN | | |
| ODN M362 | tcgtcgtcgttc:gaacgacgttgat | SEQ ID NO: 12 |
| ODN 2006 | tcgtcgttttgtcgttttgtcgtt | SEQ ID NO: 13 |
| ODN 1668 | tccatgacgttcctgatgct | SEQ ID NO: 14 |
| ODN 1826 | tccatgacgttcctgacgtt | SEQ ID NO: 15 |
| ODN 2007 | tcgtcgttgtcgttttgtcgtt | SEQ ID NO: 16 |
| ODN BW006 | tcgacgttcgtcgttcgtcgttc | SEQ ID NO: 17 |
| ODN 2395 | tcgtcgttttcggcgc:gcgccg | SEQ ID NO: 18 |
| GpC ODN (control) | | |
| ODN M362 control | tgctgctgcttg:caagcagcttgat | SEQ ID NO: 19 |
| TpC substituted | ttcttcttcttt:caatcatcttgat | SEQ ID NO: 20 |
| CpC substituted | tcctcctccttc:caaccaccttgat | SEQ ID NO: 21 |
| ODN 2006 Control | tgctgcttttgtgcttttgtgctt | SEQ ID NO: 22 |
| TpC substituted | ttcttcttttgttcttttgttctt | SEQ ID NO: 23 |
| CpC substituted | tcctcctttttgtcctttttgtcctt | SEQ ID NO: 24 |
| ODN 2007 Control | tgctgcttgtgcttttgtgctt | SEQ ID NO: 25 |
| TpC substituted | ttcttcttgttcttttgttctt | SEQ ID NO: 26 |
| CpC substituted | tcctccttgtccttttgtcctt | SEQ ID NO: 27 |

TABLE 1-continued

| | | |
|---|---|---|
| ODN BW006 Control | tgcagcttgctgcttgctgcttc | SEQ ID NO: 28 |
| TpC substituted | ttcatctttcttctttcttcttc | SEQ ID NO: 29 |
| CpC substituted | tccaccttcctccttcctccttc | SEQ ID NO: 30 |
| ODN 2395 Control | tgctgcttttgggggggcccccc | SEQ ID NO: 31 |
| TpC substituted | ttcttcttttgggggtcccccc | SEQ ID NO: 32 |
| CpC substituted | tcctccttttgggggccccccc | SEQ ID NO: 33 |
| ODN1668 Control | tccatgagcttcctgatgct | SEQ ID NO: 34 |
| TpC substituted | tccatgatcttcctgattct | SEQ ID NO: 35 |
| CpC substituted | tccatgaccttcctgatcct | SEQ ID NO: 36 |
| ODN 1826 Control | tccatgagcttcctgagctt | SEQ ID NO: 37 |
| TpC substituted | tccatgatcttcctgatctt | SEQ ID NO: 38 |
| CpC substituted | tccatgaccttcctgacctt | SEQ ID NO: 39 |

The “single-stranded ODN” according to the present invention can include ODNs having a nucleotide sequence of a CpG ODN whose CpG dinucleotide is replaced with a GpC, TpC, or CpC dinucleotide, or partial sequences thereof having an endosome delivery function.

Specific examples of such a “single-stranded ODN” can include ODNs having nucleotide sequences represented by SEQ ID NOs: 19 to 39, or nucleic acids consisting of a partial sequence thereof having 5 or more bases in length.

It should be noted that ODNs having the nucleotide sequences represented by SEQ ID NOs: 19 to 39 and having one to three, preferably one or two, more preferably one deletion, substitution, insertion, or addition can also be used as the “single-stranded ODN” according to the present invention as long as they are delivered to endosomes without TLR9 agonist activity.

The “single-stranded ODN” according to the present invention has preferably 15 or more bases in length, more preferably 15 to 28 bases in length in view of the delivery function to endosomes.

As described in Example 5 of WO2012/014945, the delivery ability to endosomes can be readily verified as follows: Transfected cells are prepared by transfection of human TLR3 together with a reporter plasmid containing an IFN-β promotor. A nucleic acid having a double-stranded RNA linked to a single-stranded ODN is added to the culture solution of the cells, and the reporter activity is compared to the control. Accordingly, persons skilled in the art could readily obtain not only the single-stranded ODNs having nucleotide sequences represented by SEQ ID NOs: 19 to 39 but also other “single-stranded ODNs” used in the present invention from the nucleotide sequences of commercially available CpG ODNs and GpC ODNs (controls) and the descriptions according to WO2012/014945 and WO2016/088784.

The single-stranded nucleotide constituting the “GpC ODN” according to the present invention is preferably modified in view of stability (nuclease resistance). Examples of such modification can include modification with phosphorothioate. The single-stranded ODN modified with phosphorothioate enables efficient delivery of the nucleic acid to endosomes without decomposed by nuclease.

(3) Synthesis of Adjuvant Nucleic Acid

The adjuvant nucleic acid according to the present invention is composed of the “double-stranded RNA” and the “single-stranded ODN” described above. The “double-stranded RNA” and the “single-stranded ODN” can be linked in any order by any method. The 5'-end of the “double-stranded RNA” may be linked to 3'-end of the “single-stranded ODN”, or the 3'-end of the “double-stranded RNA” may be linked to the 5'-end of the “single-stranded ODN”. Preferably, the 5'-end of the “double-stranded RNA” is linked to the 3'-end of the “single-stranded ODN”, and more preferably, the 3'-end of the “single-stranded ODN” is linked to the 5'-end of the sense strand of the “double-stranded RNA”.

The “double-stranded RNA” may be directly linked to the “single-stranded ODN”, or may be linked to the “single-stranded ODN” via an appropriate linker. The linker sequence can have any length (the number of bases). Other than the linker sequence, a different nucleic acid may be linked to one or both ends of the “double-stranded RNA”. In this case, the different nucleic acid is preferably linked to the 3'-end of the RNA.

Each of the single-stranded nucleic acids forming the nucleic acid according to the present invention preferably has no phosphate group linked to either end thereof. If a large amount of a nucleic acid having a residual phosphate group at the 5'-end is administrated in vivo, such a nucleic acid activates the intracytoplasmic RIG-I path to induce the production of a large amount of cytokine, causing the side effects (Robinson R A, DeVita V T, Levy H B, Baron S, Hubbard S P, Levine A S. A phase I-II trial of multiple-dose polyriboinosic-polyribocytidylic acid in patients with leukemia or solid tumors. J Natl Cancer Inst. 1976 September; 57(3):599-602). Triphosphoric acid is added to the 5'-end of an RNA strand synthesized by in vitro transcription. The nucleic acid according to the present invention can be prepared through chemical synthesis, and therefore can be synthesized as a nucleic acid having no phosphate group which links to either the 5'-end or the 3'-end thereof.

If the 3'-end of the “single-stranded ODN” is directly linked to the 5'-end of the sense strand of the “double-stranded RNA” through a covalent bond, the nucleic acid adjuvant according to the present invention can be synthesized as a nucleic acid consisting of a single-stranded nucleic acid A (chimeric nucleic acid of the “single-stranded ODN” and the sense strand of the “double-stranded RNA”) and a single-stranded nucleic acid B (antisense strand of the “double-stranded RNA”).

As one example, WO2016/088784 discloses a nucleic acid consisting of a sense strand represented by SEQ ID NO: 40 (single-stranded nucleic acid A) and an antisense strand represented by SEQ ID NO: 41 (single-stranded nucleic acid B), and its synthetic method. Although the “double-stranded RNA” is directly linked to the “single-stranded ODN” in this example, a linker may be interposed therebetween as long as it does not impart negative influences over the stability of the nucleic acid and the adjuvant activity. In this specification, the nucleic acid adjuvant consisting of the sense strand represented by SEQ ID NO: 40 and the antisense strand represented by SEQ ID NO: 41 is called "ARNAX" in some cases.

The nucleic acid according to the present invention is not limited to those consisting of the sense strand and the antisense strand. Nucleic acids composed of a sense strand and an antisense strand having a sequence identity of 80%, preferably 85%, more preferably 90%, still more preferably 95% with the sequences thereof, respectively, can also be used as the nucleic acid according to the present invention as long as they have the adjuvant activity. As described above, if the "double-stranded RNA" contains the repetition of the specific partial sequence, the repetition of the sequence identity is defined as a numeric value obtained by comparing a partial sequence to a sequence corresponding to the partial sequence.

The adjuvant activity of the nucleic acid can be verified according to Examples of WO2012/014945 and WO2016/088784, for example, primarily by preparing transfected cells through transfection of a human TLR3-espressing plasmid together with a reporter plasmid containing an IFN-β promotor into the cells, and adding a nucleic acid adjuvant to the culture solution of the cells to observe an increase in reporter activity, and more strictly by observing the tumor regression effect and the like in vivo.

The nucleic acid consisting of the sense strand and the antisense strand described above can be synthesized according to the method described in WO2016/088784, for example, by synthesizing partial sequences, and sequentially ligating the partial sequences. Off course, the nucleic acid can be synthesized by any other method than the method described above. The synthetic method may be appropriately optimized by a normal method according to the lengths and structures of the double-stranded RNA and the single-stranded ODN used.

A state of immunosuppression is generated in a tumor microenvironment by bone marrow cells invaded by tumors other than the tumor cells. Tumor-associated macrophages (TAMS) strongly support the proliferation, maintenance, and invasion of the tumors, and contribute to the formation of the microenvironment convenient for the tumors. Myeloid-derived suppressor cells (MDSCs) suppress the activity of antigen-specific T cells. If poly(I:C) therapy is performed in a cancer transplanted into mice where such a regulatory macrophage invades into tumors, the tumors regress (Shime et al. Proc. Natl. Acad. Sci. U.S.A 109(6): 2066-2071. 2012). The tumor regression is caused by the hemorrhagic necrosis of the tumors due to the production of TLR3-TICAM-1 dependent TNF-α, by TAM in response to poly(I:C). At the same time, the macrophages within the tumors are converted from a suppressor type M2 to an effector type M1, inducing an epigenetic change in TLR3 signals. It is believed that the proliferation of the tumors can be inhibited through the administration of the adjuvant composition according to the present invention as a TLR3-specific adjuvant, which can convert the cancer-suppressing cells within the tumors into a cancer-attacking type to control the microenvironment within the tumors.

The nucleic acid adjuvant according to the present invention has the following characteristics: 1) the nucleic acid is efficiently taken into dendritic cells, 2) the nucleic acid activates only TLR3 and does not activate MDA5/RIG-1, 3) the nucleic acid does not induce the production of systemic inflammatory cytokine/type I IFN, 4) the nucleic acid activates dendritic cells to induce NK cells and CTLs, 5) the nucleic acid exhibits strong antitumor activity, 6) the nucleic acid can inhibit the proliferation of tumors through control of the microenvironment within the tumors, and 7) the nucleic acid enables chemical synthesis according to the GMP standards. Accordingly, the nucleic acid adjuvant according to the present invention is significantly useful as an adjuvant for immunotherapy for cancer.

(4) Formulation

The "adjuvant composition" according to the present invention may contain pharmaceutically acceptable carriers or additives. Examples of such carriers and additives include, but should not be limited to, surfactants, fillers, colorants, fragrances, preservatives, antioxidants, stabilizers, buffers, suspensions, isotonizing agents, fillers, disintegrants, lubricants, fluidity promoters, and flavoring substances. Besides, other carriers usually used can be appropriately used. Specific examples thereof are as listed above in "Immune checkpoint blockade".

The "immune checkpoint blockade" according to the present invention can be administrated through any route. Preferred is parenteral administration. Specifically, examples thereof include injection administration, nasal administration, transpulmonary administration, and dermal administration. Examples of the injection administration include intravenous injection, intramuscular injection, intraperitoneal injection, and subdermal injection. The administration method can be appropriately selected according to the age and condition of the patient.

The dose of the "adjuvant composition" according to the present invention is appropriately determined according to the purpose of use, the administration route, and the like. If the adjuvant composition is administrated to human, the dose can be selected within the range of 0.00001 mg to 10 mg per kg of the weight per a single administration, for example. Alternatively, the dose can be selected within the range of 1 to 100 mg/body per patient, for example. However, the dose of the "adjuvant composition" according to the present invention can be used in any other dose than that above.

2.2 Antigen Molecule

The adjuvant composition according to the present invention may contain an antigen molecule. Because endogenous antigens are present in the bodies of cancer patients and bacteria-infected patients, an immune effect is obtained only by the adjuvant nucleic acid. If a sufficient effect is not obtained only by the adjuvant nucleic acid, an antigen molecule together with the adjuvant is preferably administrated according to the target disease to be treated. Examples of the antigen molecule include viral antigens, bacterial antigens, cancer antigens, and antigenic components thereof.

Examples of the viral antigens include viral antigens such as adenoviruses, retroviruses, picornaviruses, herpes viruses, rotaviruses, hantaviruses, coronaviruses, togaviruses, flaviviruses, rhabdoviruses, paramyxoviruses, orthomyxoviruses, bunyaviruses, arenaviruses, reoviruses, papillomaviruses, parvoviruses, poxviruses, hepadnaviruses, spongiform viruses, HIV, CMV, hepatitis A viruses, hepatitis B viruses, hepatitis C viruses, influenza viruses, measles viruses, polio viruses, smallpox viruses, rubella viruses, herpes simplex viruses, varicella-zoster viruses, Epstein-Barr viruses, Japanese encephalitis viruses, rabies viruses, influenza viruses, or combinations thereof.

Examples of the bacterial antigens include *Bacillus, Escherichia, Listeria, Neisseria, Nocardia, Salmonella, Staphylococcus*, and *Streptococcus* bacterial antigens or combinations thereof.

Examples of the cancer antigens include cancer antigens such as leukemia, lymphoma, astrocytoma, glioblastoma, melanoma, breast cancer, lung cancer, head and neck cancer, digestive system tumors, gastric cancer, colonic cancer, liver cancer, pancreatic cancer, uterine cancer, ovarian cancer, vaginal cancer, testicular cancer, prostate cancer, penile cancer, bone tumor, vascular tumor, esophagus cancer, rectal cancer, colon cancer, pancreatic cancer, gallbladder cancer, cholangiocarcinoma, laryngeal cancer, bronchial carcinoma, bladder cancer, kidney cancer, brain tumor, thyroid cancer, Hodgkin's disease, non-Hodgkin's lymphoma, and multiple myeloma, or combinations thereof.

The adjuvant composition according to the present invention to be used alone has a therapeutic effect to cancer or infectious disease, and the present invention also provides a medicament for treating cancer or infectious disease, the medicament comprising the adjuvant composition.

3. Medicament for Treating Cancer or Infectious Disease

The present invention provides a medicament for treating cancer or infectious disease, the medicament comprising the immune checkpoint blockade and the adjuvant composition.

The medicament according to the present invention indicates a combined medicament (for combined administration) for simultaneously, separately, or sequentially administrating the adjuvant composition to the immune checkpoint blockade containing an anti-PD-1 antibody or an anti-PD-L1 antibody.

The immune checkpoint blockade and the adjuvant composition may be separately provided, or may be provided as a kit including the immune checkpoint blockade and the adjuvant composition.

The target diseases to be treated with the medicament according to the present invention are target diseases to be treated with the immune checkpoint blockade (such as cancers and infectious diseases). Examples of the cancers include bone cancer, pancreatic cancer, skin cancer, head and neck cancer, melanoma, uterine cancer, ovarian cancer, rectal cancer, anal cancer, gastric cancer, testicular cancer, uterine cancer, fallopian tube carcinoma, endometrial carcinoma, cervix carcinoma, vaginal carcinoma, vulvar carcinoma, Hodgkin's disease, non-Hodgkin's lymphoma, esophagus cancer, small intestinal cancer, endocrine system cancer, thyroid cancer, parathyroid cancer, adrenal cancer, parenchymal sarcoma, urethral cancer, penile cancer, acute myeloid leukemia, chronic myeloid leukemia, acute lymphoblastic leukemia, chronic leukemia, acute leukemia, pediatric solid cancer, lymphocytic lymphoma, bladder cancer, kidney cancer, ureteral cancer, renal pelvic carcinoma, central nervous system (CNS) tumor, primary CNS lymphoma, tumor angiogenesis, spinal tumor, brainstem glioma, pituitary adenoma, Kaposi's sarcoma, squamous cell carcinoma, planocellular carcinoma, T cell lymphoma, and environmental tumor. In particular, the medicament can be suitably used in metastatic cancer expressing PD-L1.

Examples of the infectious diseases include HIV infection (AIDS), hepatitis, herpes, malaria, *Leishmania*, influenza, dysentery, pneumonia, tuberculosis, and sepsis. In particular, the medicament can be suitably used in HIV infection causing serious immunodeficiency.

Figure 5:
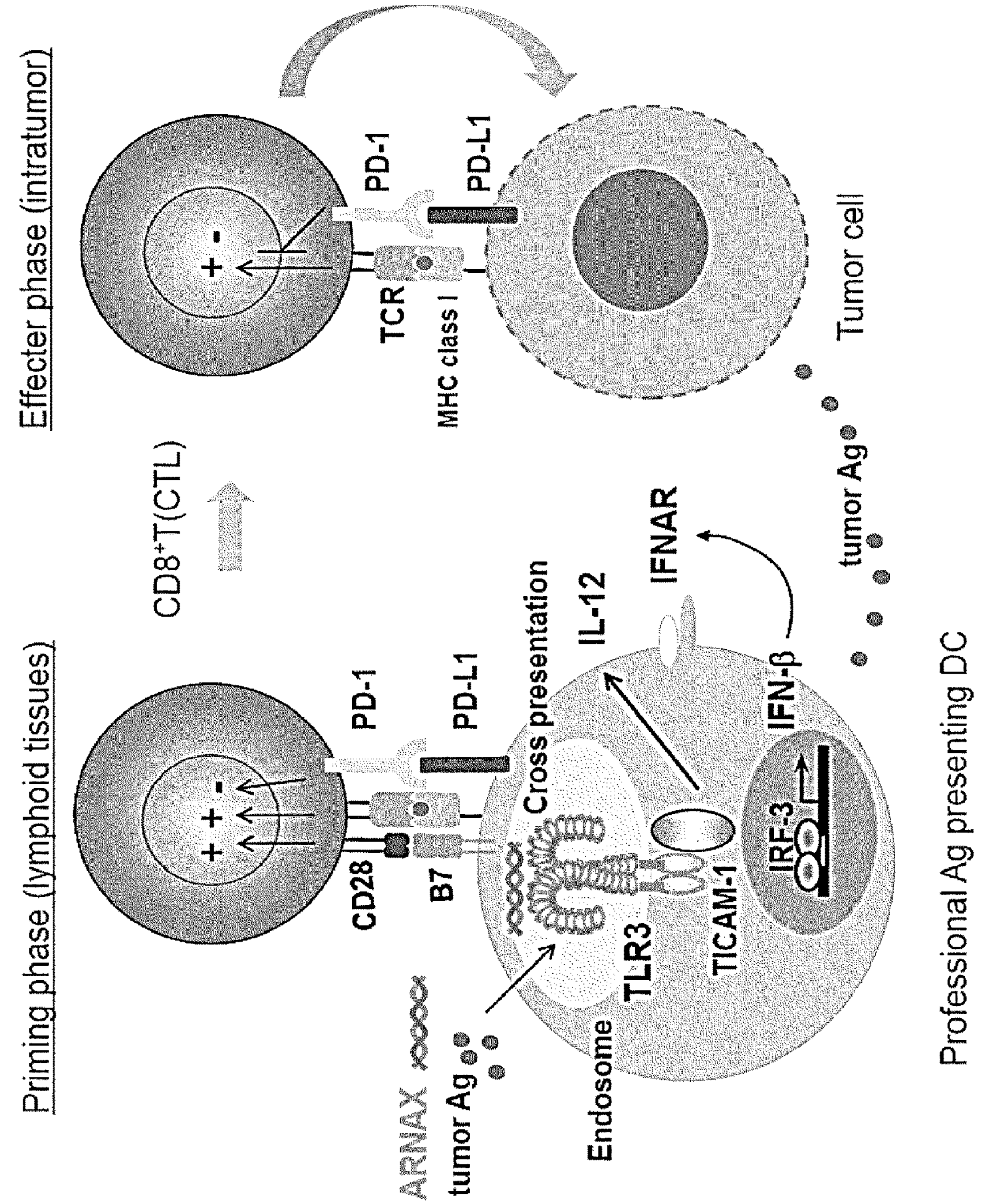
FIG. 5 illustrates a mechanism of action of the adjuvant nucleic acid (ARNAX) according to the present invention and the anti-PD-L1 antibody.

As described above, while the anti-PD-1 antibody and the anti-PD-L1 antibody act in the effector phase of the immune defense mechanism, the nucleic acid adjuvant according to the present invention is delivered to the endosomes of dendritic cells to act in the priming phase, for example, to activate TLR3 and to induce NK cells and CTLs. Accordingly, use of the adjuvant nucleic acid according to the present invention in combination with the anti-PD-1 antibody or the anti-PD-L1 antibody enables activation of the immune defense mechanism through both of the priming phase and the effector phase (see FIG. 5).

Due to the mechanism of action described above, the medicament according to the present invention, by using the adjuvant composition in combination with the anti-PD-1 antibody and the anti-PD-L1 antibody, is effective to the cancers to which the anti-PD-1 antibody or the anti-PD-L1 antibody alone is not effective, and more strongly induces the CTL-dependent tumor regression. Use of the adjuvant composition in combination with the anti-PD-1 antibody or the anti-PD-L1 antibody increases the synergistically anti-tumor effect than in the case where each of them is used alone for administration.

Furthermore, the adjuvant composition used in combination with the anti-PD-1 antibody or the anti-PD-L1 antibody can have the effects such as production of the antibody and the activation of NK cells, which cannot be provided by the anti-PD-1 antibody or the PD-L1 antibody alone, and also can have an effect such as an improvement in tumor microenvironment. The medicament according to the present invention has high safety, and can be safely administrated to elderly persons. The medicament can expand the target to be treated with the anti-PD-1 antibody or the anti-PD-L1 antibody, and can increase the therapeutic effect.

EXAMPLES

The present invention will now be described in more detail by way of Examples, but these Examples should not be construed as limitative to the present invention.

Example 1: Induction of CTLs by Administration of ARNAX and Antigen

1. Materials and Method 8 to 11-week wild type (C57BL/6) and knockout male mice (MAVS KO, MyD88 KO, TLR3 KO, TICAM-1 KO, IRF3 KO, and IRF3/7 DKO) on the B57BL/6 background were used in an experiment. PBS, OVA (100 μg), or OVA (100 μg)+ARNAX (60 μg) was subcutaneously administrated to mice on day 0 and day 7. On day 11, spleens and lymph nodes of lower limbs were collected, and the proportion of OVA-specific $CD8^+$ T cells in $CD8^+$ T cells was measured with an OVA-tetramer (made by MO BIO Laboratories, Inc.). Tetramer assay was performed according to the attached document. Specifically, spleens and lymph node cells ($1\times10^7$/ml) were dyed with an H2-Kb OVA tetramer (PE) 50× diluted for 20 minutes, and were washed, followed by dyeing with anti-CD3e mAb (APC) and anti-CD8a mAb (FITC) to analyze the proportion of OVA-specific CD8+ T cells in CD8+ T cells with a cell sorter FACSAria (BD Biosciences). Spleen cells ($1\times10^7$/ml) were stimulated with 100 nM of an OVA-specific peptide (SL8: SIINFEKL) or a control WT1 peptide (Db126: RMFPNAPYL) for three days, and the IFN-γ in the culture supernatant was measured by Cytokine bead assay (CBA; BD Biosciences).

2. Results

OVA-specific CTLs were not induced by the administration of PBS or the administration of OVA alone in the spleens and lymph nodes of lower limbs of the wild type mice. In contrast, OVA-specific CTLs were induced by the administration of OVA+ARNAX. The same results as those in the wild type mice were observed in MAVS knockout mice (where MAVS is an adaptor molecule downstream of an RIG-I-like receptor (RLR), and MyD88 knockout mice (where MyD88 is an adaptor molecule of TLRs other than TLR3. OVA-specific CTLs were not induced at all by OVA+ARNAX in knockout mice in which TLR3, TICAM-1 (adaptor molecule of TLR3), and transcription factors IRF3 and IRF7 essential to induction of Type I IFN were knockout (FIGS. 1*a* and 1*c*). A large amount of IFN-γ was produced as a result of stimulation with the OVA-specific peptide in the spleen cells of the wild type mice and the MAVS knockout mice, while the production of IFN-γ was not observed in TLR3, TICAM-1, IRF3, and IRF3/7 knockout mice at all (FIG. 1*b*).

3. Discussion

It revealed that the antigen-specific CTLs was not induced by the antigen alone, and was induced by the administration of antigen+ARNAX. The results of the knockout mice show that the induction of the antigen-specific CTLs by ARNAX is dependent on the TLR3-TICAM-1-IRF3 route, and the RLR-MAVS route and the TLR-MyD88 route excluding TLR3 is not related. The priming adjuvant activity of ARNAX can be defined as a TLR3-TICAM-1 signal.

Figure 2:
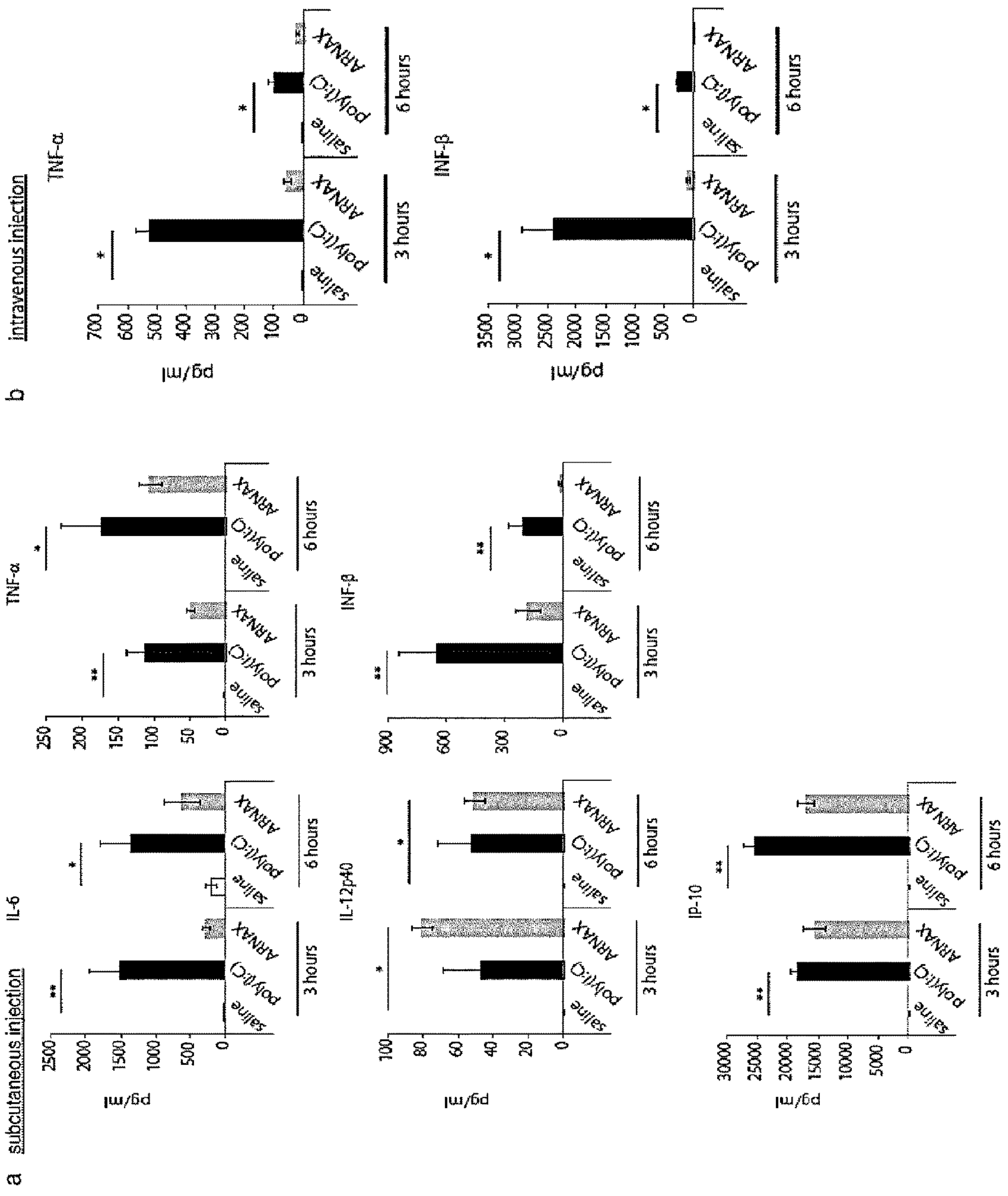
FIG. 2 illustrates the induction of cytokines when physiologic saline (control), poly(I:C), or ARNAX was given through (a) subdermal administration and (b) intravenous administration.

Example 2: Comparison of Cytokine Production Effect and Safety of ARNAX According to Administration Route 1. Materials and Method Saline, poly(I:C) (150 μg), or ARNAX (150 μg) was subcutaneously administrated to 8-week wild type (C57BL/6) female mice, or saline, poly(I:C) (50 μg), or ARNAX (50 μg) was intravenously administrated to them. Blood cytokine amount was then measured after 3 hours and 6 hours (FIG. 2). IL-6, TNF-α, and IL-12 p40 were measured by CBA and IFN-β, and IP-10 was measured by ELISA.

2. Results

Inflammatory cytokines IL-6 and TNF-α in blood in the subdermal administration of ARNAX were less than in the administration of poly(I:C). The amount of IFN-γ was also extremely small. In contrast, production of a Th1 cytokine IL-12p40 was induced more than in poly(I:C), and production of a chemokine IP-10, which recruit NK cells, NKT cells, and T cells, was induced as much as poly(I:C). In the intravenous administration, poly(I:C) strongly induced TNF-α, IL-6, and IFN-β while ARNAX barely induced these.

3. Discussion

ARNAX barely induces the production of the systemic inflammatory cytokines and type I IFN irrespective of the administration route, and therefore it is said that ARNAX is a non-inflammatory adjuvant having reduced side effects which are found in poly(I:C). In contrast, the production of the Th1 cytokine IL-12 is induced more than in poly(I:C). While antigen-specific CTL induction requires cytokines such as IL-12 and type I IFN as a third signal, there are some reports that the CTLs induced by IL-12 express PD-1 within tumors in a smaller amount than that in the CTLs induced by type I IFN and survive longer than the CTLs induced by type I IFN. Accordingly, the cytokine profile of IL-$12^{high}$/IFN-$\beta^{low}$ of ARNAX is suitable for induction of functional antigen-specific $CD8^+$ T cells within tumors.

Example 3: Antitumor Effect by Administration ARNAX and Antigen (Thymoma)

1. Materials and Method

An OVA-expressing tumor (thymoma) line EG7 ($2\times10^6$/200 μl PBS) was subcutaneously transplanted to the lower backs of C67BL/6 mice (7-week old, female). On day 7, PBS (n=5) or OVA (100 μg)+ARNAX (60 μg) (n=5) was subcutaneously administrated, and the proliferation of tumors was measured over time (FIG. 3*c*). On day 14, tumors were collected, the proportion of $CD8^+$ T cells within the tumors, and proportion of OVA-specific $CD8^+$ T cells and CD11c-positive $CD8^+$ T cells within the $CD8^+$ T cells were measured by flow cytometry (FIG. 3*d*). Tumor tissue sections thereof were prepared, and were immunostained with an anti-CD8α antibody. The invasion of $CD8^+$ T cells into the tumors was observed with a confocal microscope in the tissue sections of 20 fields of a PBS group and 16 fields of an OVA+ARNAX group, and the results were converted into numeric values (FIG. 3*f*). Furthermore, RNAs were purified from the tumor tissues with Trizol, and gene expression of Gzmb, Ifng, Perf1, Cxcl9, Cxcl10, and Cxcl11 was measured by quantitating PCR (FIG. 3*e*).

2. Results

A large amount of $CD8^+$ T cells invaded into EG7 tumors in the treatment with OVA+ARNAX (FIG. 3*d,f*). The proportion of OVA-specific CTLs in the $CD8^+$ T cells was high, and an activation marker CD11c also expressed. It is believed that tumor-reactive CTLs derived from the effector memory T cells were induced. Accompanied by this, tumor regression was induced (FIG. 3*c*). Expression of genes of granzyme (Gzmb), perforin (Prf1), IFN-γ (Ifng), Cxcl9, Cxcl10, and Cxcl11 was increased within the tumors by OVA+ARNAX (FIG. 3*e*).

3. Discussion

It is believed that the administration of ARNAX+cancer antigen can efficiently induce tumor-specific CTLs to cause the tumor-specific CTLs to invade tumors, leading to tumor regression. Expression of chemokine genes which induce cytotoxicity-associated genes of granzyme, perforin, and IFN-γ and CTLs such as Cxcl9, Cxcl10, and Cxcl11 is increased within tumors. Accordingly, ARNAX is an adjuvant which can constitute Th1 immune response within tumors.

Example 4: Administration of ARNAX in Combination with PD-L1 Antibody (Thymoma)

1. Materials and Method

Figure 4D:
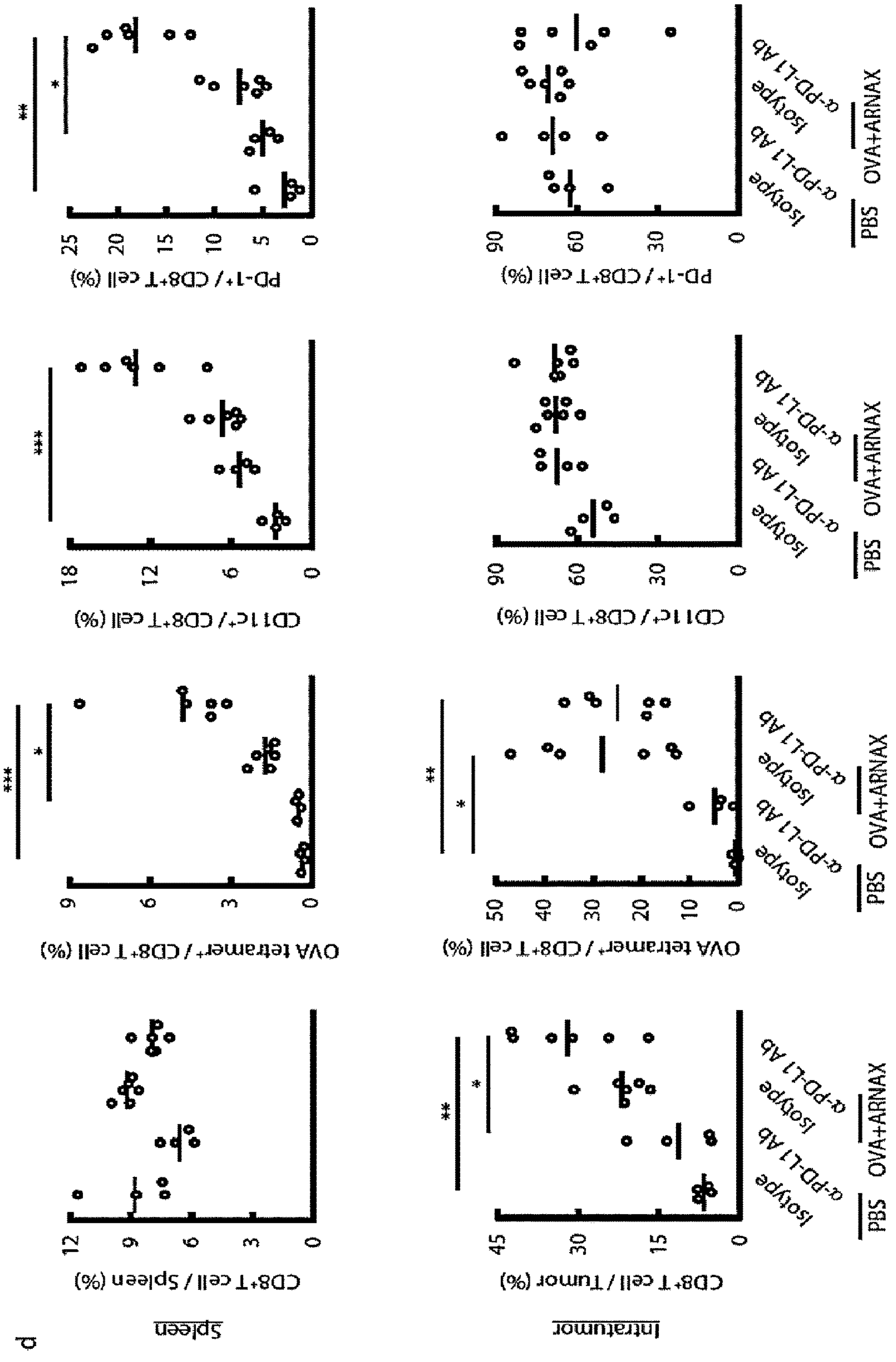
FIG. 4*d* indicates the proportions of CD8-positive T cells (left), OVA tetramer-positive/CD8-positive T cells (left center), CD11c-positive/CD8-positive T cells (right center), PD-1-positive/CD8-positive T cells (right) in spleens and tumors of mice to which PBS (control) or OVA+ARNAX was subcutaneously administrated, and the anti-mice PD-L1 antibody or an isotype antibody was intravenously administration (the upper row indicates the proportions in the spleens, and the lower row indicates the proportions in the intratumors).
Figure 4E:
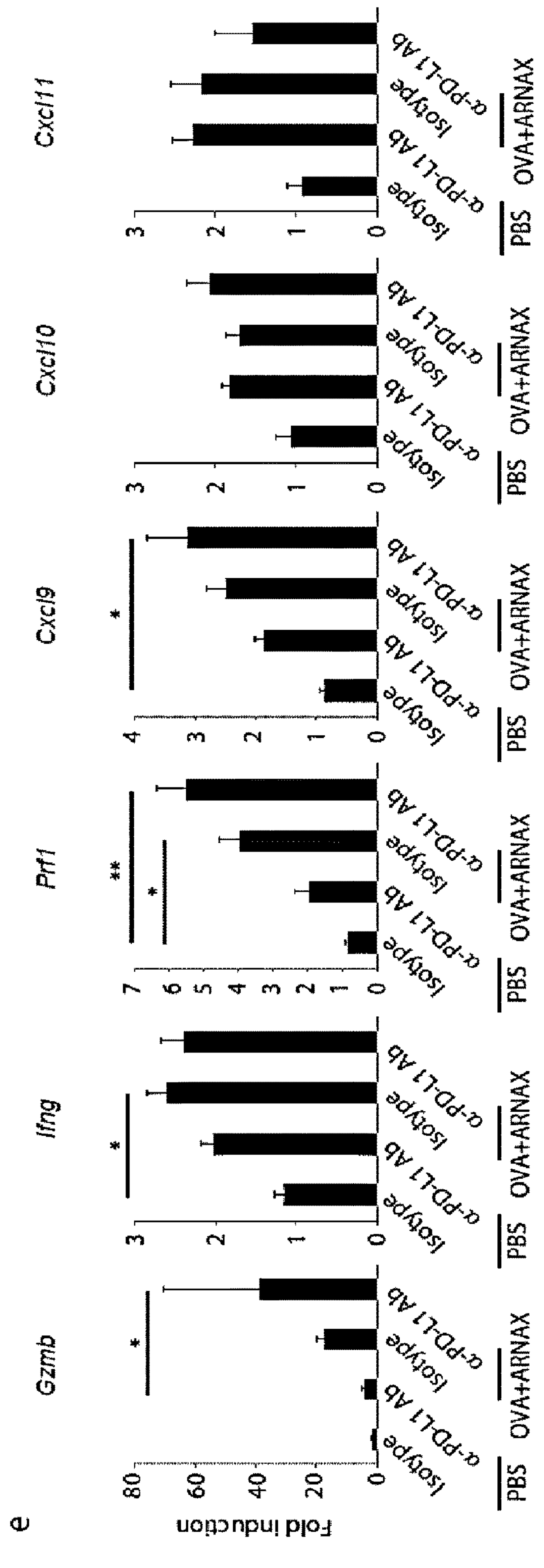
FIG. 4*e* illustrates the results of analysis by RT-PCR of the induction of expression of Gzmb, Ifng, Prf1, Cxcl9, Cxcl10, and Cxcl11 in tumors of mice to which PBS (control) or OVA+ARNAX was subcutaneously administrated, and an anti-mice PD-L1 antibody or isotype antibody was intravenously administrated.

PD-L1 highly expressing EG7 (Kataoka et al., Nature 534:402, 2016) ($2\times10^6$/200 μl PBS) was subcutaneously transplanted to the lower backs of C67BL/6 mice (7-week old, female). On day 7, PBS (isotype Ab group) (n=4), PBS (anti-PD-L1 Ab group) (n=4), OVA (100 μg)+ARNAX (60 μg) (isotype Ab group) (n=6), or OVA (100 μg)+ARNAX (60 μg) (anti-PD-L1 Ab group) (n=6) was subcutaneously administrated to the mice. On days 7, 9, and 11, isotype Ab or anti-PD-L1 Ab (200 μg/head) was intravenously administrated, and the proliferation of tumors was measured over time (FIG. 4*c*). On day 13, spleens and tumors were collected. The proportions of $CD8^+$ T cells within the spleens and the tumors, and the proportions of OVA-specific $CD8^+$ T cells, CD11c-positive $CD8^+$ T cells, and PD-1-positive $CD8^+$ T cells within the $CD8^+$ T cells were measured by flow cytometry (FIG. 4*d*). Furthermore, RNAs were purified from the tumor tissues with Trizol, and expression of genes of Gzmb, Ifng, Perf1, Cxcl9, Cxcl10, and Cxcl11 was measured by quantitating PCR (FIG. 4*e*).

2. Results

Tumor proliferation was not suppressed by treatment with a PD-L1 antibody alone in PD-L1 highly expressing EG7 while tumor regression was induced by OVA+ARNAX. Furthermore, tumors more effectively regressed by use of OVA+ARNAX in combination with a PD-L1 antibody (FIG. 4*c*). CD8+ T cells invaded tumors in the administration of OVA+ARNAX, and a larger amount of T cells invaded tumors in the administration of OVA+ARNAX in combination with the anti-PD-L1 antibody. The proportion of OVA-specific CD8+ T cells within the tumors was high in both of OVA+ARNAX and OVA+ARNAX+anti-PD-L1 Ab (FIG. 4*d*). In contrast, the proliferation of antigen-specific CD8+ T cells significantly increased in the spleens by use in combination with the PD-L1 antibody. It also turned out that the proportions of the activation marker CD11c and the PD-1-positive CD8+ T cells were high, and tumor reactive CTLs derived from effector memory T cells were induced. Expression of genes of Gzmb, Ifng, Perf1, and Cxcl9 within the tumors also was increased by use of ARNAX+OVA in combination with the anti-PD-L1 antibody (FIG. 4*e*).

3. Discussion

While the proliferation of tumors in the PD-L1 high expressing EG7 tumors resistant to the treatment with the PD-L1 antibody was suppressed to some extent by the administration of OVA+ARNAX, tumor regression could be effectively introduced by use thereof in combination with the anti-PD-L1 antibody. Accordingly, it is believed that the PD-1/PD-L1 resistance can be cancelled.

It is believed that by blocking the PD-1 route, a large amount of tumor-specific CTLs was induced in the priming phase to invade tumors, and the cancel of suppression of functions in the effector phase caused effective cancer regression. Accordingly, use of ARNAX+OVA in combination with the anti-PD-1/PD-L1 antibody is useful in reinforcing the action of ARNAX (see FIG. 5).

Example 5: Administration of ARNAX in Combination with PD-L1 Antibody (Melanoma)

1. Materials and Method

Figure 6F:
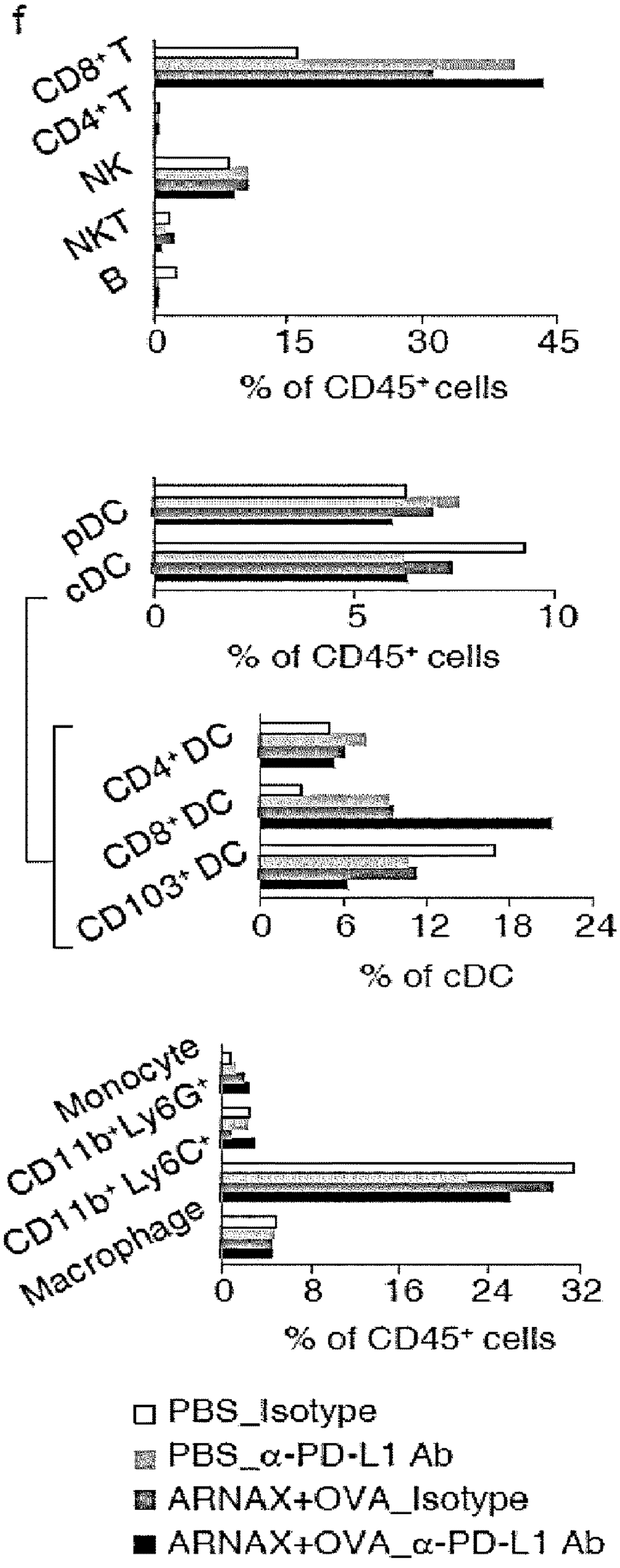
FIG. 6*f* shows the proportion of tumor-invaded immune cells. The proportion of tumor-invaded lymphocytes gated by CD45-positive cells (top), the proportion of a dendritic cell (DC) subset gated with CD45-positive cells, and the proportion of tumor-invaded Monocyte gated with CD45-positive cells, a CD11b-positive bone marrow cell subset, and macrophages.

An OVA expressing B16 melanoma line MO5 ($2\times10^6$/200 μl PBS) was subcutaneously transplanted into the lower backs of C67BL/6 mice (7-week old, female). On day 10, PBS (isotype Ab group) (n=5), PBS (anti-PD-L1 Ab group) (n=4), OVA (100 μg)+ARNAX (60 μg) (isotype Ab group) (n=4), or OVA (100 μg)+ARNAX (60 μg) (anti-PD-L1 Ab group) (n=4) was subcutaneously administrated. On days 10, 12, 14, and 16, isotype Ab or anti-PD-L1 Ab (200 μg/head) was intravenously administrated, and the proliferation of tumors was measured over time (FIG. 6*c*). On day 17, spleens and tumors were collected, and the proportions of $CD8^+$ T cells in the spleens and the tumors, and the proportions of OVA-specific $CD8^+$ T cells, CD11c-positive $CD8^+$ T cells, and PD-1-positive $CD8^+$ T cells in the $CD8^+$ T cells were measured by flow cytometry (FIG. 6*d*). RNAs were purified from the tumor tissues with Trizol, and expression of genes of granzyme (Gzmb), perforin (Prf1), IFN-γ (Ifng), and Cxcl10 was measured by quantitative PCR (FIG. 6*e*). Furthermore, the proportions of tumor-invaded immune cells, i.e., lymphocytes, dendritic cells, and CD11b-positive bone marrow cells each were measured (FIG. 6*f*).

2. Results

The administration of OVA+ARNAX induces tumor regression in PD-L1 expressing MO5 as much as in the administration of the PD-L1 antibody alone. Further, use of OVA+ARNAX in combination with the PD-L1 antibody more effectively regressed tumors (FIG. 6*c*). CD8+ T cells invaded tumors in the administration of OVA+ARNAX, and a larger amount of T cells invaded tumors in use thereof in combination with the anti-PD-L1 antibody. The proportion of OVA-specific CD8+ T cells in the tumors was high in both of the administration of OVA+ARNAX and that of OVA+ARNAX+anti-PD-L1 Ab (FIG. 6*d*). In contrast, the proliferation of antigen-specific CD8+ T cells in the spleens was significantly increased by use of OVA+ARNAX in combination with the PD-L1 antibody. It turned out that the proportions of an activation marker CD11c and PD-1-positive CD8+ T cells were also high, and tumor reactive CTLs derived from effector memory T cells were induced. Expression of genes of Gzmb, Ifng, Perf1, and Cxcl9 within the tumors was increased by used of ARNAX+OVA in combination with the anti-PD-L1 antibody (FIG. 6*e*).

3. Discussion

While tumor proliferation is suppressed in the MO5 tumor by the treatment with ARNAX+cancer antigen, use thereof in combination with the PD-L1 antibody can more effectively lead to tumor regression. From this, it is believed that the PD-1/PD-L1 immune checkpoint blockade used in combination with ARNAX+cancer antigen can demonstrate a high antitumor effect also to melanoma.

Example 6: Structure of ARNAX and IFNβ Activation Ability Via TLR3

1. Materials and Method

The following four double-stranded RNAs were synthesized.

ARNAX140: double-stranded RNA having a nucleotide sequence of positions 1 to 140 of SEQ ID NO: 1

ARNAX120 #1: double-stranded RNA having a nucleotide sequence of positions 17 to 136 of SEQ ID NO: 1

ARNAX120 #2: double-stranded RNA having a sequence in which a nucleotide sequence of positions 17 to 56 of SEQ ID NO: 1 is linked three times ARNAX130: double-stranded RNA having a nucleotide sequence of positions 1 to 130 of SEQ ID NO: 1

Figure 7:
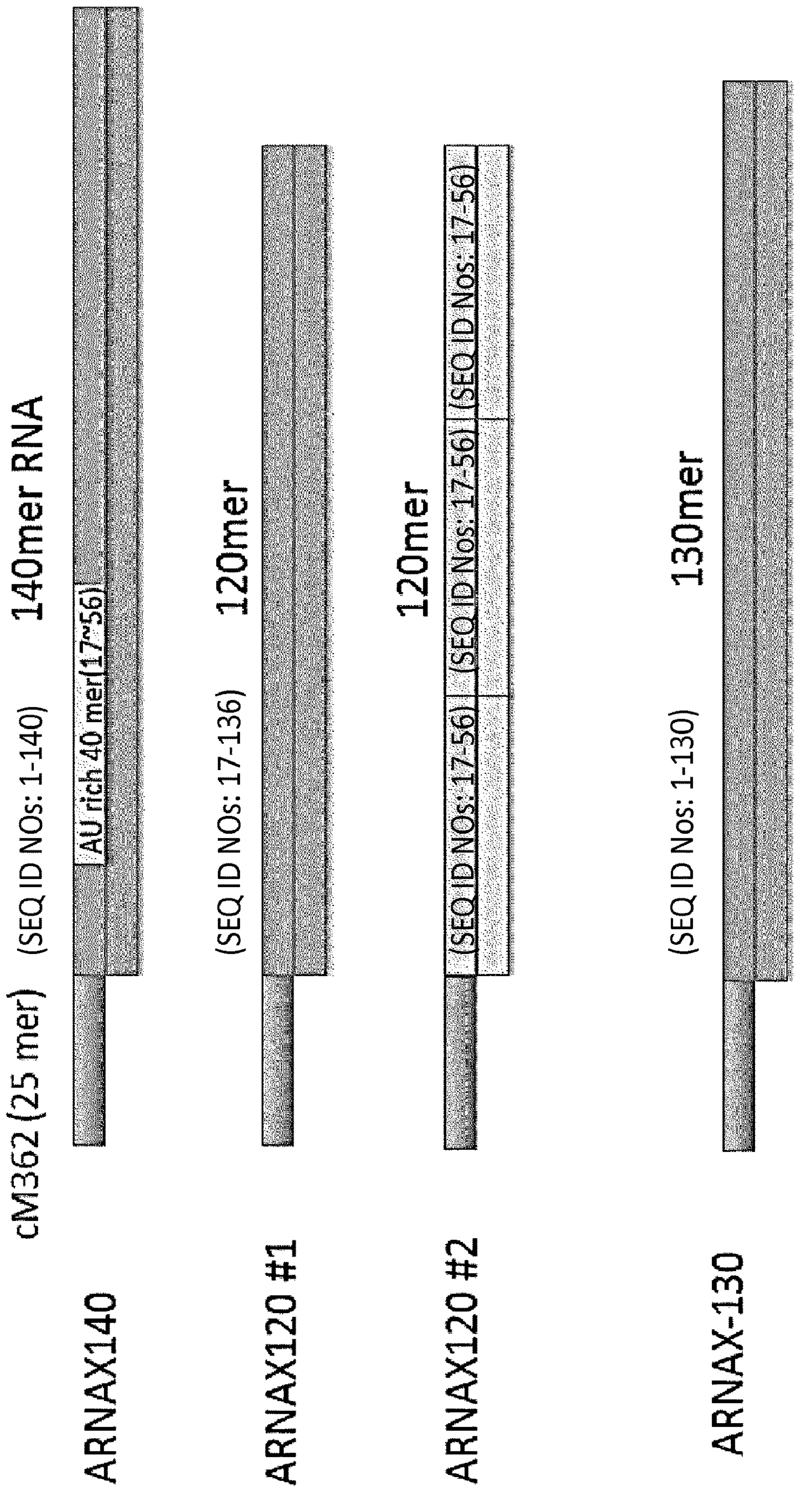
FIG. 7 shows the structures of ARNAX120 #1, ARNAX #2, ARNAX130, and ARNAX140.

The positions 17 to 56 of SEQ ID NO: 1 are an AU-rich region (FIG. 7).

Figure 8:
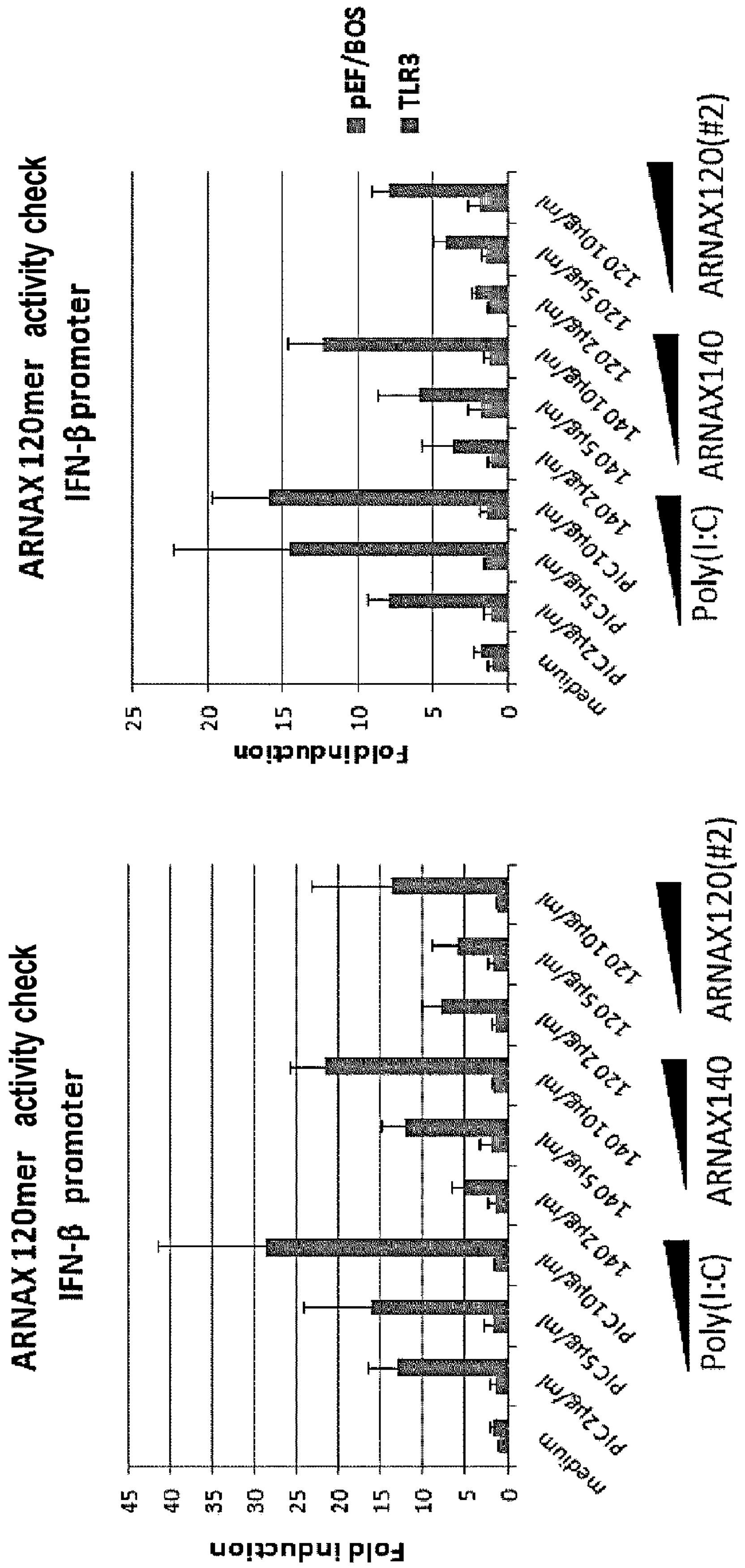
FIG. 8 shows the IFN-β promotor activation ability via TLR3 of ARNAX120 #2.

A control plasmid (pEF/BOS) or a human TLR3 expressing plasmid together with an IFN-β promotor reporter plasmid was transfected into HEK293 cells. After 24 hours, a culture medium, poly(I:C), ARNAX140, or ARNAX120 #2 was added in a concentration of 2, 5, or 10 μg/ml. The luciferase activity in the cells was measured after 6 hours. The luciferase activity was expressed as a fold of the luciferase activity (defined as 1) of the culture medium as a negative control added to pEF/BOS expressing cells (FIG. 8).

Figure 9:
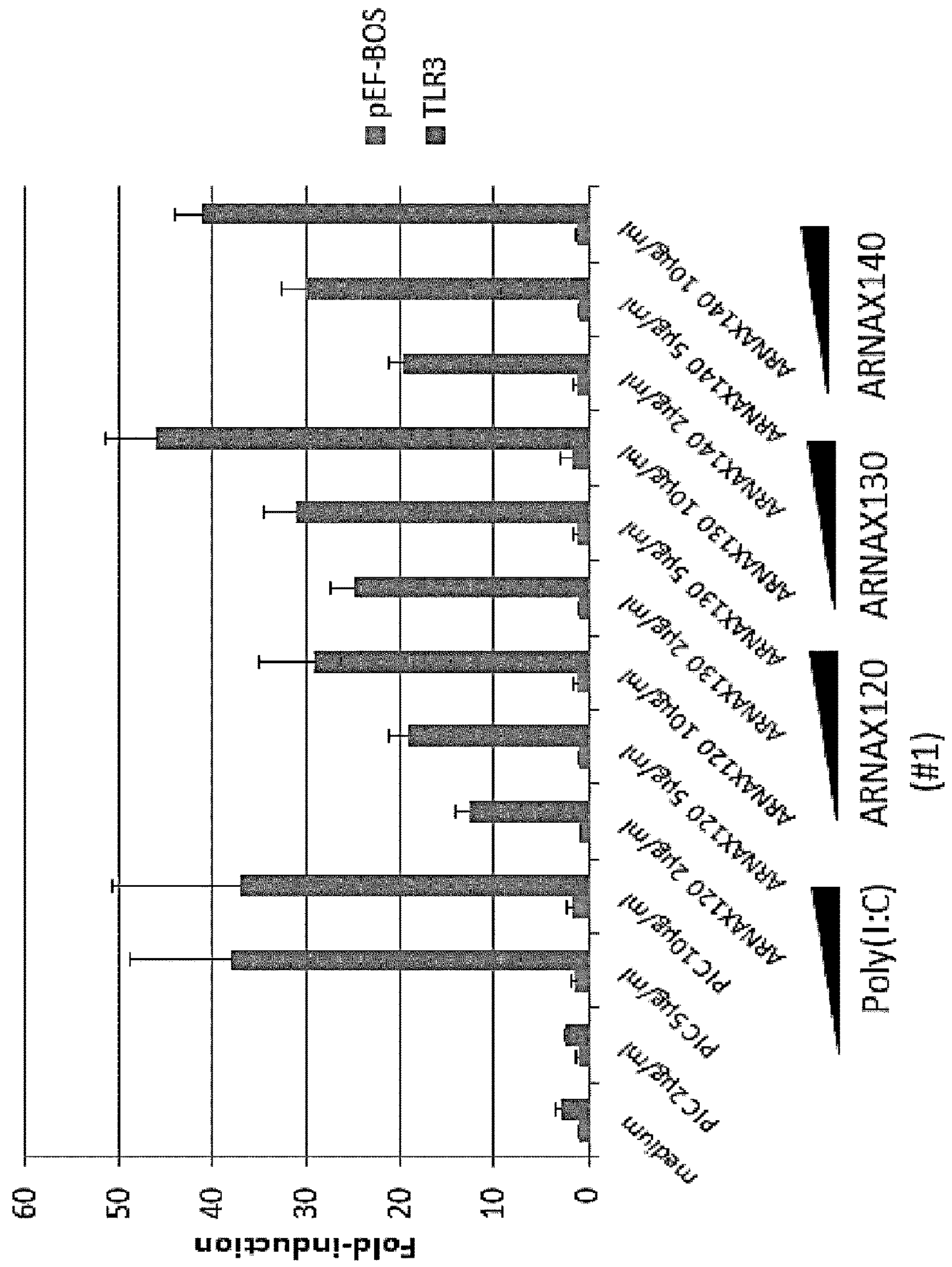
FIG. 9 shows the IFN-β promotor activation ability via TLR3 of ARNAX120 #1 and that of ARNAX130.

The same experiment was performed by adding poly(I:C), ARNAX140, ARNAX130, or ARNAX120 #1 to the cells in a concentration of 2, 5, or 10 μg/ml (FIG. 9).

2. Results

The IFN-β promotor activation ability via TLR3 of ARNAX120 was 70 to 80% of that via ARNAX140, and no difference in TLR3 activation ability between ARNAX120 #1 and ARNAX120 #2 having different RNA sequences was found. It was verified that ARNAX130 has an IFN-β promotor activation ability via TLR3 identical to that of ARNAX140.

Example 7: Induction Activity of CTLs of ARNAX120

1. Materials and Method

According to Example 1, PBS, OVA (100 μg), OVA (100 μg)+poly(I:C) (50 μg), OVA (100 μg)+ARNAX140 (10 μg), OVA (100 μg)+ARNAX140 (30 μg), or OVA (100 μg)+ARNAX140 (60 μg) was subcutaneously administrated to 8-week wild type (C57BL/6) female mice, and the proportion of OVA-specific $CD8^+$ T cells was measured in spleens and lymph nodes of lower limbs.

Similarly, PBS, OVA (100 μg), OVA (100 μg)+poly(I:C) (50 μg), OVA (100 μg)+ARNAX120 #2 (10 μg), or OVA (100 μg)+ARNAX120 #2 (30 μg) was subdermal administrated to 8-week wild type (C57BL/6) female mice, and the proportion of OVA-specific $CD8^+$ T cells was measured in the spleens. The spleen cells ($1\times10^7$/ml) were stimulated with 100 nM of an OVA-specific peptide (SL8: SIINFEKL) or a control WT1 peptide (Db126: RMFPNAPYL) for three days, and IFN-γ in the culture supernatant was measured by ELISA.

2. Results

Figure 10:
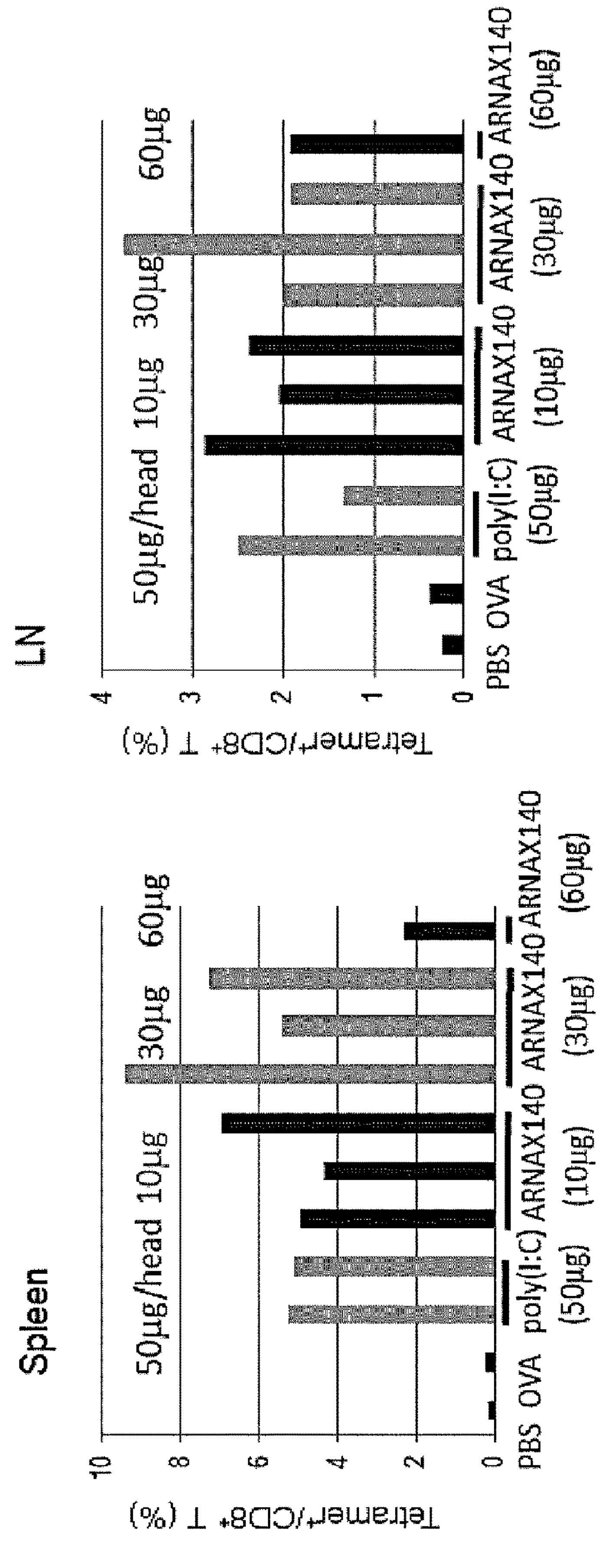
FIG. 10 shows the in vivo cross-priming activity of ARNAX140 (the dose was varied).
Figure 11:
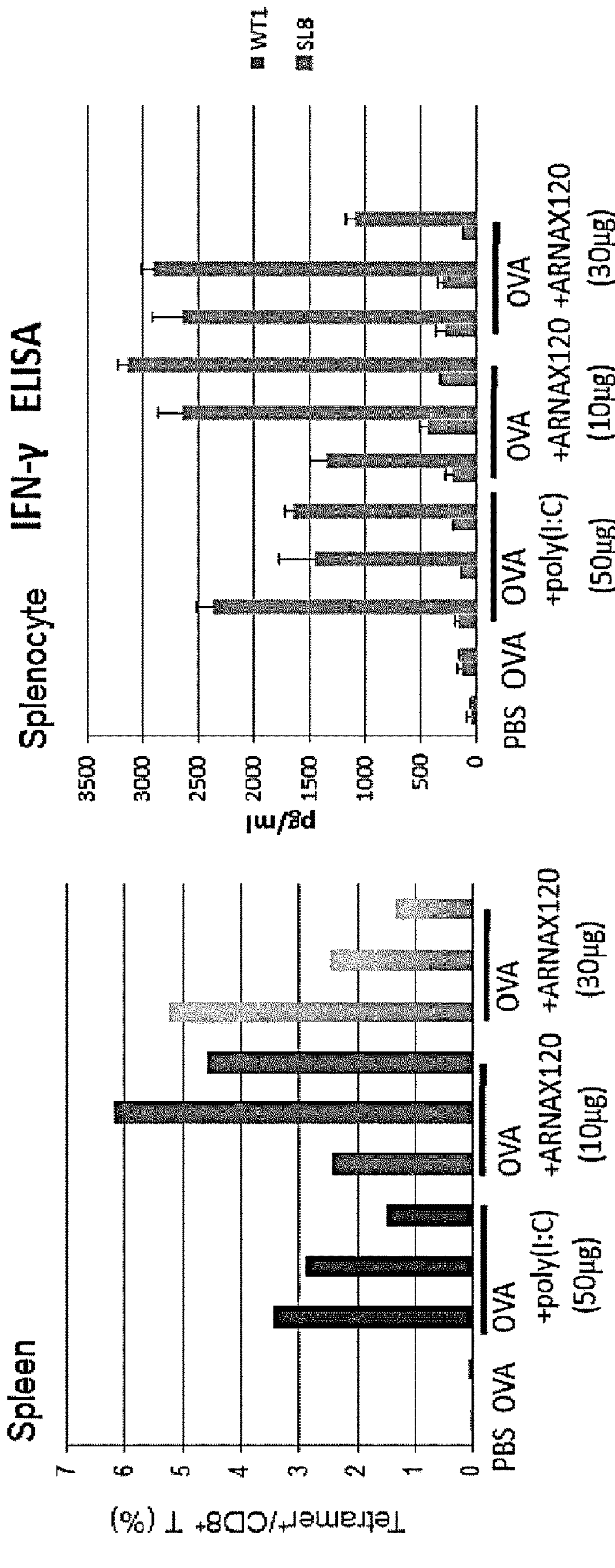
FIG. 11 illustrates of the in vivo cross-priming activity of ARNAX120 #2 (the dose was varied).

While OVA-specific CTLs were not induced by administration of PBS or OVA alone, the administration of OVA+poly(I:C), CTLs were induced by the administration of OVA+ARNAX140 and OVA+ARNAX120 #2. Thus, in vivo cross-priming activity was verified (FIG. 10, FIG. 11). Varying the dose of ARNAX140 revealed that a dose of 10 μg/head provides sufficient CTL induction activity (FIG. 10). It was verified that ARNAX120 had a CTL induction activity (cross-priming activity) identical to that of ARNAX140, and exhibited sufficient CTL induction activity at a dose of 10 μg/head (FIG. 11).

Example 8: Antitumor Activity of ARNAX120

1. Materials and Method

According to Example 3, EG7 ($2\times10^6$/200 μl PBS) was subcutaneously transplanted to the lower backs of C67BL/6 mice (7-week old, female). On day 7, PBS (n=5), ARNAX120 #1 (10 μg) (n=4), or OVA (100 μg)+ARNAX120 #1 (10 μg) (n=5) was subcutaneously administrated, and the proliferation of tumors was measured over time.

2. Results

Figure 12:
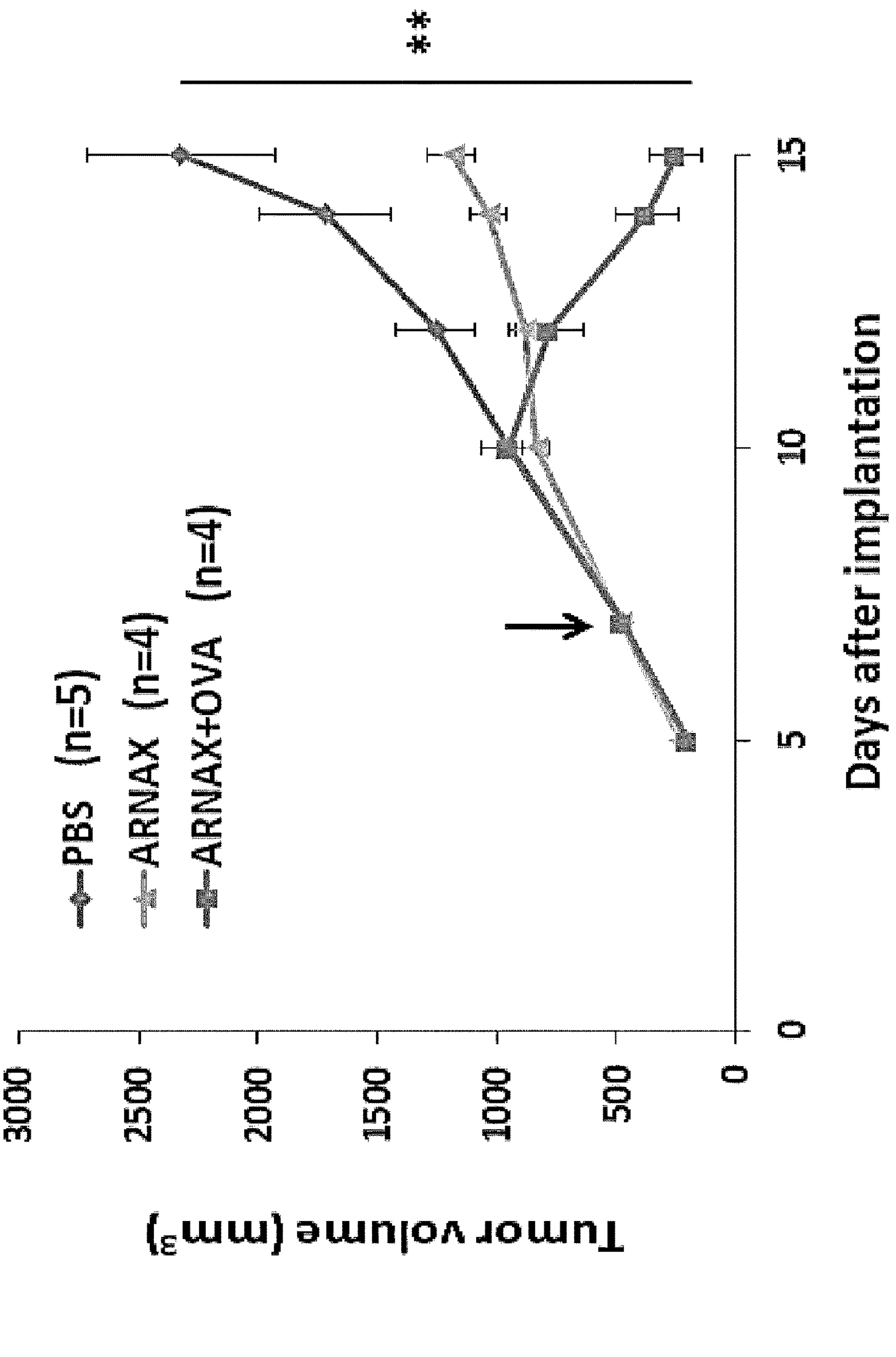
FIG. 12 illustrates the antitumor effect (EG7) of ARNAX120 #1.

While suppression of proliferation of EG7 tumors was observed in the administration of ARNAX120 #1 (10 μg) alone, it was verified that the tumors were significantly regressed by the simultaneous administration with the OVA antigen (FIG. 12). From these results, it was verified that ARNAX having at least 120 bases in length can demonstrate a sufficient effect, and the sequence contains at least 40 continuous bases of the sequence represented by SEQ ID NO: 1. A shorter nucleic acid is preferred because of the production efficiency and cost. Accordingly, ARNAX120 and ARNAX130 can be useful adjuvant candidates for practical use.

INDUSTRIAL APPLICABILITY

The present invention can improve the effects and response rate of the PD-1/PD-L1 antibody therapy. Accordingly, the present invention is useful in the medical field in which the immunotherapy for cancer and infectious diseases using an immune checkpoint blockade (PD-1/PD-L1 antibody) is expected.

All the publications, patents, and patent applications cited herein are incorporated herein as they are, by reference.

SEQUENCE LISTING FREE TEXT

SEQ ID NO: 12: synthetic DNA (ODN M362)

SEQ ID NO: 13: synthetic DNA (ODN 2006)

SEQ ID NO: 14: synthetic DNA (ODN 1668)

SEQ ID NO: 15: synthetic DNA (ODN 1826)

SEQ ID NO: 16: synthetic DNA (ODN 2007)

SEQ ID NO: 17: synthetic DNA (ODN BW006)

SEQ ID NO: 18: synthetic DNA (ODN 2395)

SEQ ID NO: 19: synthetic DNA (ODN M362 control)

SEQ ID NO: 20: synthetic DNA (ODN M362 control_TpC substituted)

SEQ ID NO: 21: synthetic DNA (ODN M362 control_CpC substituted)

SEQ ID NO: 22: synthetic DNA (ODN 2006 control)

SEQ ID NO: 23: synthetic DNA (ODN 2006 control_TpC substituted)

SEQ ID NO: 24: synthetic DNA (ODN 2006 control_CpC substituted)

SEQ ID NO: 25: synthetic DNA (ODN 2007 control)

SEQ ID NO: 26: synthetic DNA (ODN 2007 control_TpC substituted)

SEQ ID NO: 27: synthetic DNA (ODN 2007 control_CpC substituted)

SEQ ID NO: 28: synthetic DNA (ODN BW006 control)

SEQ ID NO: 29: synthetic DNA (ODN BW006 control_TpC substituted)

SEQ ID NO: 30: synthetic DNA (ODN BW006 control_CpC substituted)

SEQ ID NO: 31: synthetic DNA (ODN 2395 control)

SEQ ID NO: 32: synthetic DNA (ODN 2395 control_TpC substituted)

SEQ ID NO: 33: synthetic DNA (ODN 2395 control_CpC substituted)

SEQ ID NO: 34: synthetic DNA (ODN 1668 control)

SEQ ID NO: 35: synthetic DNA (ODN 1668 control_TpC substituted)

SEQ ID NO: 36: synthetic DNA (ODN 1668 control_CpC substituted)

SEQ ID NO: 37: synthetic DNA (ODN 1826 control)

SEQ ID NO: 38: synthetic DNA (ODN 1826 control_TpC substituted)

SEQ ID NO: 39: synthetic DNA (ODN 1826 control_CpC substituted)

SEQ ID NO: 40: DNA for sense strand/RNA chimeric molecule (ARNAX140)

SEQ ID NO: 41: synthetic RNA for antisense strand (ARNAX140)

SEQ ID NO: 42: DNA for sense strand/RNA chimeric molecule (ARNAX120 #1)

SEQ ID NO: 43: synthetic RNA for antisense strand (ARNAX120 #1)

SEQ ID NO: 44: DNA for sense strand/RNA chimeric molecule (ARNAX120 #2)

SEQ ID NO: 45: synthetic RNA for antisense strand (ARNAX120 #2)

SEQ ID NO: 46: DNA for sense strand/RNA chimeric molecule (ARNAX130)

SEQ ID NO: 47: synthetic RNA for antisense strand (ARNAX130)

The invention claimed is:

1. A method for treating cancer or infectious disease, comprising administering an immune checkpoint blockade and an adjuvant composition to a patient in need thereof, wherein the immune checkpoint blockade comprises an anti-PD-1 antibody or an anti-PD-L1 antibody, the adjuvant composition comprises a nucleic acid adjuvant comprising (i) a double-stranded RNA having a TLR3 activation ability, and (ii) a single-stranded oligodeoxynucleotide (single-stranded ODN) that is delivered to a dendritic cell endosome, wherein the double-stranded RNA has a nucleotide sequence comprising a sequence of continuous 40 or more bases of a nucleotide sequence represented by SEQ ID NO:1 and having a total length of 100 to 160 bases in length, and the single-stranded ODN consists of a sequence of a CpG ODN where CpG is replaced with GpC, TpC, or CpC, or a partial sequence thereof having 15 or more bases in length, wherein the immune checkpoint blockade and the adjuvant are the sole active agents administered and results in activation of TLR3 to endosomes and/or induce tumor-specific CTLs to cause the tumor-specific CTLs to invade tumors, leading to tumor regression.

2. The method according to claim 1, wherein the immune checkpoint blockade and the adjuvant composition are separately administered.

3. The method according to claim 1, wherein the immune checkpoint blockade and the adjuvant composition are simultaneously administered.

4. The method according to claim 1, wherein the immune checkpoint blockade and the adjuvant composition are sequentially administered.

5. The method according to claim 1, wherein the adjuvant composition comprises an antigen molecule selected from the group consisting of bacterial antigen, viral antigens, and cancer antigen.

6. The method according to claim 1, wherein the nucleic acid adjuvant comprises a nucleic acid having a non-phosphorylated end.

7. The method according to claim 1, wherein the double-stranded RNA is a nucleic acid having a nucleotide sequence represented by one of SEQ ID NOs: 2 to 11, a nucleic acid having a nucleotide sequence having continuous 100 or more bases thereof.

8. The method according to claim 1, wherein the double-stranded RNA is a nucleic acid having a nucleotide sequence represented by SEQ ID NO: 11, a nucleic acid having a nucleotide sequence having continuous 100 or more bases thereof.

9. The method according to claim 1, wherein the single-stranded ODN is a nucleic acid consisting of a nucleotide sequence represented by one of SEQ ID NOs: 19 to 39 or a partial sequence thereof having 5 or more bases in length.

10. The method according to claim 1, wherein the single-stranded ODN is a nucleic acid consisting of a nucleotide sequence represented by one of SEQ ID NOs: 19 to 24 or a partial sequence thereof having 5 or more bases.

11. The method according to claim 1, wherein the single-stranded ODN has 15 to 28 bases in length.

12. The method according to claim 1, wherein the single-stranded ODN comprises a nucleotide modified with phosphorothioate.

13. The method according to claim 1, wherein the nucleic acid adjuvant is a nucleic acid comprising a sense strand represented by SEQ ID NO: 40 and an antisense strand represented by SEQ ID NO: 41, a nucleic acid comprising a sense strand represented by SEQ ID NO: 42 and an antisense strand represented by SEQ ID NO: 43.

14. The method according to claim 1, wherein the nucleic acid adjuvant comprises:

1) a sense strand represented by SEQ ID NO: 40 and an antisense strand represented by SEQ ID NO: 41;

2) a sense strand represented by SEQ ID NO: 42 and an antisense strand represented by SEQ ID NO: 43;

3) a sense strand represented by SEQ ID NO: 44 and an antisense strand represented by SEQ ID NO: 45, or 4) a sense strand represented by SEQ ID NO: 46 and an antisense strand represented by SEQ ID NO: 47.

15. The method according to claim 1, wherein the cancer is a tumor that is not treated with the anti-PD-L1 antibody alone.

16. The method according to claim 1, wherein the cancer is metastatic cancer expressing PD-L1.

17. The method according to claim 1, wherein the double-stranded RNA has a total length of 110 to 150 bases.

* * * * *